US008431561B2

(12) United States Patent
Boss et al.

(10) Patent No.: US 8,431,561 B2
(45) Date of Patent: Apr. 30, 2013

(54) METHODS AND COMPOSITIONS FOR TREATMENT OF EXCESS NITRIC OXIDE OR CYANIDE TOXICITY

(75) Inventors: Gerry Boss, La Jolla, CA (US); Vijay Sharma, Encinitas, CA (US); Kate E. Broderick, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 743 days.

(21) Appl. No.: 11/630,049

(22) PCT Filed: Jun. 17, 2005

(86) PCT No.: PCT/US2005/021535
§ 371 (c)(1),
(2), (4) Date: May 2, 2008

(87) PCT Pub. No.: WO2006/009874
PCT Pub. Date: Jan. 26, 2006

(65) Prior Publication Data
US 2008/0227746 A1    Sep. 18, 2008

Related U.S. Application Data

(60) Provisional application No. 60/581,207, filed on Jun. 18, 2004.

(51) Int. Cl.
*A61K 31/555* (2006.01)
*A61K 31/70* (2006.01)

(52) U.S. Cl.
USPC ............................................ 514/186; 514/52

(58) Field of Classification Search .................. 514/186, 514/52
See application file for complete search history.

(56) References Cited

U.S. PATENT DOCUMENTS 4,451,571 A   5/1984  Allen ............................ 436/505

FOREIGN PATENT DOCUMENTS

WO    WO 95/31204 A1   11/1995

OTHER PUBLICATIONS

Gunasekar et al, "Cyanide-Induced Neurotoxicity Involves Nitric Oxide and Reactive Oxygen Species Generation After N-Methyl-d-aspartate Receptor Activation", The Journal of Pharmacology and Experimental Therapeutics, vol. 277, No. 1, 1996, pp. 150-155.*
Abou-Seif, "Blood Antioxidant Status and Urine Sulfate and Thiocyanate Levels in Smokers," *J. Biochem. Toxicol.*, 1997, 11(3), 133-138.
Alarie, "Toxicity of Fire Smoke," *Crit Rev. Toxicol.*, 2002, 32(4), 259-289.
Alcorta, "Smoke Inhalation & Acute Cyanide Poisoning," *JEMS*, 2004, 29, 6-15.
Baker et al., "Determination of Metabolically Active $B_{12}$ and Inactive $B_{12}$ Analog Titers in Human Blood Using Several Microbial Reagents and Radiodilution Assay," *J. Am. Coll. Nutr.*, 1986, 5, 467-475.
Baldwin et al., "The Chemistry of Vitamin $B_{12}$: Part 20; Diaquocobinamide: p$K$ Values and Evidence for Conformational Isomers," *J. Chem. Soc. Dalton Trans.*, 1983, 217-223.
Baud et al., "Elevated Blood Cyanide Concentrations in Victims of Smoke Inhalation," *N. Engl. J. Med.*, 1991, 325, 1761-1766.
Boss et al., "Decreased Purine Synthesis during Amino Acid Starvation of Human Lymphoblasts," *J. Biol. Chem.*, 1982, 257(8), 4242-4247.
Boss, "Decreased Phosphoriboylpyrophosphate As the Basis for Decreased Purine Synthesis during Amino Acid Starvation of Human Lymphoblasts," *J. Biol. Chem.*, 1984, 259(5), 2936-2941.
Braun et al., "Evaluation of the Renal Toxicity of Heme Proteins and Their Derivatives: A Role in the Genesis of Acute Tubule Necrosis," *J. Exp. Med.*, 1970, 131, 443-460.
Broderick et al., "Interactions between epithelial nitric oxide signaling and phosphodiesterase activity in Drosophila," *Am. J. Physiol.*, 2003, 285, C1207-C1218.
Broderick, K. et al., "Nitric Oxide Scavenging by the Cobalamin Precursor Cobinamide," *J. of Biological Chemistry*, 2005, 280(10), 8678-8685.
Carterson et al., "The Transcriptional Regulator AlgR Controls Cyanide Production in *Pseudomonas aeruginosa*," *J. Bacteriol.*, 2004, 186(20), 6837-6844.
Chen et al., "Synergism between Calcium and Cyclic GMP in Cyclic AMP Response Element-Dependent Transcriptional Regulation requires Cooperation between CREB and C/EBPβ," *Mol. Cell. Biol.*, 2003, 23(12), 4066-4082.
Chowdhury et al., "Role of the Dimethylbenzimidazole Tail in the Reaction Catalyzed by Coezyme $B_{12}$-Dependent Methylmalonyl-CoA Mutase," *Biochemistry*, 1999, 38, 15287-15294.
Clancy et al., "Nitric Oxide: A Novel Mediator of Inflammation," *Proc. Soc. Exp. Biol. Med.*, 1995, 210, 93-101.
Coates et al., "The Activity for Chicks of some Bitamin $B_{12}$-like Compounds," *Biochem.J.*, 1956, 64, 682-686.
Cobb, "Use of nitric oxide synthase inhibitors to treat septic shock: The light has changed from yellow to red," *Crit. Care Med.*, 1999, 27(5), 855-856.
Cummings, "The treatment of cyanide poisoning," *Occup. Med. (Lond)*, 2004, 54, 82-85.
Danishpajooh et al., "Nitric Oxide Inhibits Methionine Synthase Activity in Vivo and Disrupts Carbon Flow through the Folate Pathway," *J. Biol. Chem.*, 2001, 276(29), 27296-27303.
Dow et al., "Integrative Physiology and Functional Genomics of Epithelial Function in a Genetic Model Organism," *Physiol Rev.*, 2003, 83, 687-729.
Eckstein, "Cyanaide as a Chemical Terrorism Weapon," *JEMS*, 2004, 29, 22-31.

(Continued)

*Primary Examiner* — Elli Peselev
(74) *Attorney, Agent, or Firm* — Fenwick & West LLP

(57) ABSTRACT

Methods for treating disease states in a subject caused or exacerbated by the presence of excess nitric oxide (NO) or excess cyanide are provided. Methods for alleviating the symptoms of a disease state in a subject caused or exacerbated by the presence of excess nitric oxide (NO) or excess cyanide in the subject are also provided. Pharmaceutical compositions comprising cobinamide and a pharmaceutically acceptable carrier are also provided.

30 Claims, 14 Drawing Sheets

OTHER PUBLICATIONS

El Kholty et al., "Portal and Biliary Phases of Enterohepatic Circulation of Corrinoids in Humans," *Gastroenterology*, 1991, 101, 1399-1408.

El Mabrouk et al., "Antiproliferative effect of L-NAME on rat vascular smooth muscle cells," *Life Sci.*, 2000, 67, 1613-1623.

Elfering et al., "Biochemistry of mitochondrial nitric-oxide synthase," *J. Biol. Chem.*, 2002, 277, 38079-38086.

Ermens et al., "Significance of elevated cobalamin (vitamin B12) levels in blood," *Clin. Biochem.*, 2003, 36, 585-590.

Esposito et al., "Inhalation Toxicity of Carbon Monoxide and Hydrogen Cyanide Gases Released During the Thermal Decomposition of Polymers," *J. Fire Sci.*, 1988, 6, 195-242.

Exner et al., "Thiocyanate Catalyzes Myeloperoxidase-Initiated Lipid Oxidation in LDL," *Free Radic. Biol. Med.*, 2004, 37(2), 146-155.

Fedosov et al., "Binding of Balamin and Cobinamide to Transcobalamin from Bovine Milk," *Biochemistry*, 1995, 34, 16082-16087.

Fedosov et al., "Comparative Analysis of Cobalamin Binding Kinetics and Ligand Protection for Intrinsic Factor, Transcobalamin, and Haptocorrin," *J. Biol. Chem.*, 2002, 277(12), 9989-9996.

Ford et al., "Separation and study of corrinoid cobalt-ligand isomers by high-performance liquid chromatorgraphy," *J. Chromatogr.*, 1991, 536, 185-191.

Ford et al., "The Preparation and Characterization of the Diaquo-Forms of Several Incomplete Corrinoids: Cobyric Acid, Cobinamide, and Three Isomeric Cobinic Acid Pentaamides," *J. Inorg. Biochem.*, 1991, 41, 235-244.

Forsyth et al., "Hydroxocobalamin as a cyanide antidote: safety, efficacy and pharmacokinetics in heavily smoking normal volunteers," *J. Toxicol. Clin. Toxicol.*, 1993, 31(2), 277-294.

Fortin et al., "Hydroxocobalamin: Treatment for Smoke Inhalation-Associated Cyanide Poisoning," *JEMS*, 2004, 29, 18-21.

Garvey et al., "Potent and Selective Inhibition of Human Nitric Oxide Synthases," *J. Biol. Chem.*, 1994, 269(43), 26669-26676.

Gewitz et al., "Cyanide Formation in Preparations from *Chlorella vulgaris* Beijerinck: Effect of Sonication and Amygdalin Addition," *Planta (Berl.)*, 1976, 131, 145-148.

Gracia et al., "Cyanide Poisoning and Its Treatment," *Pharmacotherapy*, 2004, 24(10), 1358-1365.

Greenberg et al., "Hydroxocobalamin (Vitamin B12a) Prevents and Reverses Endotoxin-Induced Hypotension and Mortality in Rodents: Role of Nitric Oxide," *J. Pharmacol. Exp. Ther.*, 1995, 273(1), 257-265.

Greenfield et al., "Microbiological, Biological, and Chemical Weapons of Warfare and Terrorism," *Am.J.Med.Sci.*, 2002, 323(6), 326-340.

Gudi et al., "Regulation of Gene Expression by cGMP-dependent Protein Kinase," *J. Biol. Chem.*, 1996, 271(9), 4597-4600.

Guilbault et al., "Ultra Sensitive, Specific Method for Cyanide Using $p$-Nitrobenzaldehyde and o-Dinitrobenzene," *Anal. Chem.*, 1966, 28, 834-836.

Ha et al., "Nitric oxide prevents 6-hydroxydopamine-induced apoptosis in PC12 cells through cGMP-dependent PI3 kinase/Akt activation," *FASEB J.*, 2003, 17, 1036-1047.

Hall et al., "Hycroxyhcoalamin / Sodium Thiosulfate as a Cyanide Antidote," *J. Emerg. Med.*, 1987, 5, 115-121.

Hallemeesch et al., "Differential effects of selective and non-selective NOS inhibition on renal arginine and protein metabolism during endotoxemia in rats," *Clin. Nutr.*, 2002, 21(2), 111-117.

Harbrecht et al., "Inhibition of nitric oxide synthesis during endotoxemia promotes intrahepatic thrombosis and an oxygen radical-mediated hepatic injury," *J. Leukoc. Biol.*, 1992, 52, 390-394.

Hasuike et al., "Accumulation of cyanide and thiocyanate in haemodialysis patients," *Nephrol. Dial. Transplant.*, 2004, 19(6), 1474-1479.

Hayward et al., "The Chemistry of Vitamin $B_{12}$: Part IV. The Thermodynamic trans-Effect," *J. Chem. Soc.*, 1965, 6485-6493.

Heneka et al., "Polymerized Hemoglobin Restores Cardiovascular and Kidney Funtion in Endotoxin-induced Shock in the Rat," *J. Clin. Invest*, 1997, 99(1), 47-54.

Hochman, "Cardiogenic Shock Complicating Acute Myocardial Infarction: Expanding the Paradigm," *Circulation*, 2003, 107, 2998-3002.

Hölsher, "Nitric oxide, the enigmatic neuronal messenger: its role in synaptic plascticity," *Trends Neurosci.*, 1997, 20(7), 298-303.

Hotchkiss et al., "Inhibition of NO synthesis in septic shock," *Lancet*, 1992, 339, 434-435.

Ichinose et al., "A selective inducible NOS dimerization inhibitor prevents systemic, cardiac, and pulmonary hemodynamic dysfunction in endotoxemic mice," *Am. J. Physiol.*, 2003, 285, H2524-H2530.

Idriss et al., "Nitric Oxide Regulation of Gene Transcription via Soluble Guanylate Cyclase and Type I cGMP-dependent Protein Kinase," *J. Biol. Chem.*, 1999, 274(14), 9489-9493.

Kanazawa et al., "Binding of Cobalamin Analogs to Intrinsic Factor—Cobalamin Receptor and Its Prevention by R Binder," *Proc. Soc. Exp. Biol. Med.*, 1986, 183, 333-338.

Kikuchi et al., "Assay of emthylmalonyl CoA mutase with high-performance liquid chromatography," *Clin. Chim. Acta*, 1989, 184, 307-314.

Kim et al., "Nitric Oxide Scavenging, Alone or with Nitric Oxide Synthesis Inhibition, Modulates Vascular Hyporeactivity in Rats with Intraperitoneal Sepsis," *Shock*, 2002, 17(5), 423-426.

Kim et al., "Regulation of Integrin $\alpha_v\beta_3$-mediated Enothelial Cell Migration and Angiogenesis by Integrin $\alpha_5\beta_1$ and Protein Kinase A," *J Biol. Chem.*, 2000, 275(43), 33920-33928.

Kolhouse et al., "Absorption, Plasma Transport, and Cellular Retention of Cobalamin Analogues in the Rabbit: Evidence for the Existence of Multiple Mechanisms that Prevent the Absorption and Tissue Dissemination of Naturally Occurring Cobalamin Analogues," *J. Clin. Invest*, 1977, 60, 1381-1392.

Kolhouse et al., "Mechanism of Conversion of Human Apo- to Holomethionine Synthase by Various Forms of Cobalamin," *J. Biol. Chem.*, 1991, 266(34), 23010-23015.

Kolhouse et al., "Cobalamin Analogues are Present in Human Plasma and Can Mask Cobalamin Deficiency because Current Radioisotope Dilution Assays are not Specific for True Cobalamin," *N. Engl. J. Med.*, 1978, 299(15), 785-792.

Komeno et al., "Role of Nitric Oxide in Hemodialysis-Related Hypotension in an Experimental Renal Dysfuntion Dog Model," *J. Vet. Med. Sci.*, 2004, 66(1), 53-57.

Kondo et al., "Effects of cobalamin, cobalamin analogues and cobalamin binding proteins on $P388D_1$ mouse leukemic cells in culture," *Int. J. Hematol.*, 1992, 56, 167-177.

Kondo et al., "Presence and Formation of Cobalamin Analogues in Multivitamin-Mineral Pills," *J. Clin. Invest*, 1982, 70, 889-898.

Kondo et al., "Presence of Cobalamin Analogues in Animal Tissues," *PNAS U.S.A*, 1980, 77, 817-821.

Liaudet et al., "Nonselective versus Selective Inhibition of Inducible Nitric Oxide Synthase in Experimental Endotoxic Shock," *J. Infect. Dis.*, 1998, 177, 127-132.

Lloyd-Jones et al., "The Vascular Biology of Nitric Oxide and Its Role in Atherogenesis," *Annu. Rev. Med.*, 1996, 47, 365-375.

Megarbane et al., "Antidotal Treatment of Cyanide Poisoning," *J. Chin Med. Assoc.*, 2003, 66, 193-203.

Menezes et al., "A novel nitric oxide scavenger decreases liver injury and improve survival after hemorrhagic shock," *Am. J. Physiol.*, 1999, 277, G144-G151.

Michigami et al., "Determination of Thiocyanate in Human Serum by Ion Chromatography," *Analyst*, 1988, 113, 389-392.

Moncada et al., "The L-Arginine-Nitric Oxide Pathway," *New Eng. J. Med.*, 1993, 329, 2002-2012.

Moncada et al., "Nitric Oxide: Physiology, Pathophysiology and Pharmacology," *Pharmacol. Rev.*, 1991, 43(2), 109-142.

Moore et al., "Antidotal Use of Methemoglobin Forming Cyanide Antagonists in Concurrent Carbon Monoxide/Cyanide Intoxication," *J. Pharmacol. Exp. Ther.*, 1987, 242(1), 70-73.

Morbidelli et al., "Nitric oxide mediates mitogenic effect of VEGF on coronary venular endothelium," *Am. J. Physiol.*, 1996, 270, H411-415.

Morin et al., "Differential expression of inducible nitric oxide synthase messenger RNA along the longitudinal and crypt-villus axes of the intestine in endotoxemic rats," *Crit Care Med.,* 1998, 26(7), 1258-1264.

Mushett et al., "Antidotal Efficacy of Vitamin $B_{12}$ (Hydroxo-Cobalamin) in Experimental Cyanide Poisoning," *Proc. Soc. Exp. Biol. Med.,* 1952, 81, 234-237.

Nadler et al., "Scavenging nitric oxide reduces hepatocellular injury after endotoxin challenge," *Am. J. Physiol.,* 2001, 281, G173-G181.

Nathan, "Nitric oxide as a secretory product of mammalian cells," *FASEB J.,* 1992, 6, 3051-3064.

Nedvetsky et al., "There's NO binding like NOS binding: Protein-protein interactions in NO/cGMP signaling," *PNAS U.S.A,* 2002, 99, 16510-16512.

O'Kane, "Modelling human diseases in *Drosophila* and *Caenorhabditis*," *Semin. Cell Dev. Biol.,* 2003, 14, 3-10.

Oltean et al., "Nutritional Modulation of Gene Expression and Homocysteine Utilization by Vitamin $B_{12}$," *J. Biol. Chem.,* 2003, 278(23), 20778-20784.

Panda et al., "Kinetics and Mechanism for the binding of HCN to Cytochrome *c* Oxidase," *Biochemistry,* 1995, 34, 10009-10018.

Pfeilschifter et al., "Regulation of gene expression by nitric oxide," *Pflugers Arch.,* 2001, 442, 479-486.

Poon et al., "Complexity of Inducible Nitric Oxide Synthase: Cellular Source Determines Benefit Versus Toxicity," *Circulation,* 2003, 108, 1107-1112.

Posner et al., "Hydroxocobalamin Therapy of Cyanide Intoxication in Guinea Pigs," *Anesthesiology,* 1976, 44(2), 157-160.

Price et al., "Type II nitric oxide synthase activity is cardio-protective in experimental sepsis," *Eur. J. Pharmacol.,* 2003, 472, 111-118.

Reinhard et al., "Actin-based motility: stop and go with Ena/VASP proteins," *Trends Biochem. Sci.,* 2001, 26(4), 243-249.

Riedel et al., "Co-ordinate variations in methylmalonyl-CoA mutase and methionine synthase, and the cobalamin cofactors in human glioma cells during nitrous oxide exposure and the subsequent recovery phase," *Biochem. J.,* 1999, 341, 133-138.

Rotenberg, "Cyanide as a Weapon of Terror," *Pediatr. Ann.,* 2003, 32(4), 236-240.

Saavedra-Molina et al., "Mitochondrial nitric oxide inhibits ATP synthesis: Effect of free calcium in rat heart," *Amino Acids,* 2003, 24, 95-102.

Salkowski et al., "Cyanide Poisoning in Animals and Humans: A Review," *Vet. Hum. Toxicol.,* 1994, 36, 455-466.

Scanlon et al., "Evidence for more extensive deposits of epitopes of oxidized low density lipoprotein in aortas of young people with elevated serum thiocyanate levels," *Atherosclerosis,* 1996, 121, 23-33.

Shah et al., "Nitric Oxide in Gastrointestinal Health and Disease," *Gastroenterology,* 2004, 126, 903-913.

Sharma, V. et al., "Reactions of Nitric Oxide with Vitamin $B_{12}$ and Its Precursor, Cobinamide," *Biochemistry,* 2003, 42, 8900-8908.

Shultz et al., "Endogenously Synthesized Nitric Oxide Prevents Endotoxin-induced Glomerular Thrombosis," *J. Clin .Invest,* 1992, 90, 1718-1725.

Silverman et al., "Cyanide Toxicity in Burned Patients," *J. Trauma,* 1988, 28(2), 171-176.

Soderberg et al., "Respiration-Deficient Chinese Hamster Cell Mutants: Genetic Characterization," *Somat. Cell Genet.,* 1979, 5(2), 225-240.

Spain et al., "Nitric Oxide Synthase Inhibition Aggravates Intestinal Microvascular Vasoconstriction and Hypoperfusion of Bacteremia," *J. Trauma,* 1994, 36(5), 720-725.

Stabler et al., "Inhibition of Cobalamin-dependent Enzymes by Cobalamin Analogues in Rats," *J. Clin. Invest.,* 1991, 87, 1422-1430.

Szabo et al., "Beneficial Effects and Improved Survival in Rodent Models of Septic Shock with S-Methylisothiourea Sulfate, a Potent and Selective Inhibitor of Inducible Nitric Oxide Synthase," *PNAS U.S.A,* 1994, 91, 12472-12476.

Tickoo et al., "*Drosophila melanogaster* as a model system for drug discovery and pathway screening," *Curr. Opin. Pharmacol.,* 2002, 2, 555-560.

Tribl et al., "Effect of nitric oxide on capillary hemodynamics and cell injury in the pancreas during Pseudomonas pneumonia-induced sepsis," *Am. J. Physiol,* 2004, 286, H340-H345.

van Buuren et al., "Biochemical and Biophysical Studies on Cytochrome $aa_3$; VI. Reaction of Cyanide with Oxidized and Reduced Enzyme," *Biochim. Biophys. Acta,* 1972, 256, 258-276.

van Dalen et al., "Substrates and products of eosinophil peroxidase," *Biochem. J.,* 2001, 358, 233-239.

Vincent et al., "Effects of Nitric Oxide in Septic Shock," *Am. J. Respir. Crit. Care Med.,* 2000, 161, 1781-1785.

Way, "Cyanide Intoxication and its Mechanism of Antagonism," *Annu. Rev. Pharmacol. Toxicol.,* 1984, 24, 451-481.

Weinberg et al., "Cobalamin Inhibition of HIV-1 Integrase and Integration of HIV-1 DNA into Cellular DNA," *Biochem. Biophys. Res. Commun.,* 1998, 246, 393-397.

Weissbach et al., "Studies on the Terminal Reaction in the Biosynthesis of Methionine," *J. Biol. Chem.,* 1963, 238(10), 3318-3324.

Willard et al., "Rapid Prenatal and Postnatal Detection of Inborn Errors of Propionate, Methylmalonate, and Cobalamin Metabolism: A Sensitive Assay Using Cultured Cells," *Hum. Genet.,* 1976, 32, 277-283.

Wright et al., "Protective and pathological roles of nitric oxide in endotoxin shock," *Cardiovasc. Res.,* 1992, 26, 48-57.

Yadava et al., "Species-specific and mutant MWFE proteins; Their effect on the assembly of a functional mammalian mitochondrial complex I," *J. Biol. Chem.,* 2002, 277(45), 21221-21230.

Zerbe et al., "Use of vitamin $B_{12}$ in the treatment and prevention of nitroprusside-induced cyanide toxicity," *Crit. Care Med.,* 1993, 21(3), 465-467.

Zhang et al., "Defects in leukocyte-mediated initiation of lipid peroxidation in plasma as studied in myeloperoxidase-deficient subjects: systematic identification of multiple endogenous diffusible substrates for myeloperoxidase in plasma," *Blood,* 2002, 99(5), 1802-1810.

Zhuang et al., "Vasodilator-stimulated Phosphoprotein Activation of Serum-response Element-dependent Transcription Occurs Downstream of RhoA and is Inhibited by cGMP-dependent Protein Kinase Phosphorylation," *J. Biol. Chem.,* 2004, 279(11), 10379-10407.

Chinese Second Office Action, Chinese Application No. 200580027058.4, May 21, 2010, 6 pages.

Chinese First Office Action, Chinese Application No. 200580027058.4, Aug. 21, 2009, 8 pages.

Chinese Office Action, Chinese Application No. 200580027058.4, Jan. 18, 2011, 10 pages.

Brenner, M. et al., "Comparison of Cobinamide to Hydroxocobalamin in Reversing Cyanide Physiologic Effects in Rabbits Using Diffuse Optical Spectroscopy Monitoring," Journal of Biomedical Optics, Jan./Feb. 2010, pp. 017001-1-017001-8, vol. 15, No. 1.

Broderick, K.E. et al., "The Cobalamin Precursor Cobinamide Detoxifies Nitroprusside-Generated Cyanide," Experimental Biology and Medicine, 2007, pp. 789-798, vol. 232.

Cambal, L.K. et al., "Acute, Sublethal Cyanide Poisoning in Mice is Ameliorated by Nitrite Alone: Complications Arising from Concomitant Administration of Nitrite and Thiosulfate as an Antidotal Combination," Chemical Research in Toxicology, May 2, 2011, pp. 1104-1112, vol. 24.

Chan, A. et al., "Cobinamide is Superior to Other Treatments in a Mouse Model of Cyanide Poisoning," Clinical Toxicology, 2010, pp. 709-717, vol. 48.

Pearce, L.L. et al., "Antagonism of Nitric Oxide Toward the Inhibition of Cytochrome *c* Oxidase by Carbon Monoxide and Cyanide," Chem. Res. Toxicol., 2008, pp. 2073-2081, vol. 21, No. 11.

Pearce, L.L. et al., "Reversal of Cyanide Inhibition of Cytochrome *c* Oxidase by the Auxiliary Substrate Nitric Oxide," The Journal of Biological Chemistry, Dec. 26, 2003, pp. 52139-52145, vol. 278, No. 52.

\* cited by examiner

METHODS AND COMPOSITIONS FOR TREATMENT OF EXCESS NITRIC OXIDE OR CYANIDE TOXICITY

CROSS-REFERENCE TO RELATED APPLICATIONS

This application is the National Phase of International Application No. PCT/US2005/021535 filed Jun. 17, 2005, which claims the benefit of U.S. Provisional Patent Application No. 60/581,207, filed Jun. 18, 2004, the disclosures of which are incorporated herein by reference in their entirety.

STATEMENT REGARDING FEDERALLY SPONSORED RESEARCH OR DEVELOPMENT

This invention was made with Government support of Grant No. AI 064368 awarded by the National Institutes of Health. The Government has certain rights in this invention.

FIELD

This invention generally relates to cobinamide and biologically active derivatives and analogs of cobinamide that modulate nitric oxide (NO) or excess cyanide levels in patients. The invention further relates to pharmaceutical compositions containing cobinamide and biologically active derivatives and analogs of cobinamide, and methods of use thereof.

BACKGROUND

Nitric oxide (NO) is an important signaling molecule, and a number of NO synthesis inhibitors and scavengers have been developed to allow study of NO functions, and to reduce excess NO levels in disease states.

Septic shock is characterized by refractory hypotension, and has an extremely high mortality rate. Various cytokines and signaling molecules contribute to the septic state, with nitric oxide (NO) playing a major role in the development of the hypotension. NO is produced by three different NO synthases: neuronal NOS (nNOS), inducible NOS (iNOS), and endothelial NOS (eNOS). A marked induction of iNOS is largely responsible for the increased NO levels in sepsis. Non-selective NOS inhibitors showed some success in animal models of sepsis, but in a large Phase III trial one of these agents resulted in side effects and increased mortality. Selective iNOS inhibitors have shown more promise in animal models, but have yet to be tried in humans. Another approach to lower NO levels in sepsis is to use an NO scavenger, and several NO scavengers including hemoglobin, dithiocarbamate derivatives, and vitamin $B_{12}$ (cobalamin) have been shown to be beneficial in animal models of sepsis. Cobalamin had been previously demonstrated to bind NO, and thereby inhibit the vitamin $B_{12}$-dependent enzyme methionine synthetase (Danishpajooh, *J. Biol. Chem.* 276:27296-27303, 2001).

Cyanide is a highly toxic agent which inhibits mitochondrial cytochrome c oxidase, thereby depleting cellular ATP. It contributes to smoke inhalation deaths in fires, and could be used as a weapon of mass destruction. Cyanide is generated in household fires due to the high amount of plastic material that is usually present. Cobalamin has been used to treat cyanide toxicity in Europe, and although it has been shown to be highly effective, it has not been used in this country. Similarly, carbon monoxide (CO) is generated in fires and the most common cause of death in fires is smoke inhalation, and in particular inhalation of cyanide and CO.

Therefore, it would be desirable to provide new methods and compositions for preventing and treating excess nitric oxide or excess cyanide in subjects with no adverse side effects. The methods and pharmaceutical compositions of the present invention are directed toward these, as well as other, important ends.

SUMMARY

The present invention provides methods for preventing and treating excess nitric oxide or excess cyanide in a patient. More specifically, the present invention relates to methods of preventing and treating a disease state or alleviating the symptoms of a disease state in a patient caused or exacerbated by the presence of excess nitric oxide or excess cyanide in the patient. The present invention also provides pharmaceutical compositions.

In one aspect, a method for treating a disease state in a subject caused or exacerbated by the presence of excess nitric oxide (NO) in the subject is provided comprising: administering a pharmaceutically effective amount of cobinamide, or a biologically active derivative or analog thereof, to the subject. In some methods, the disease state is sepsis, chronic liver failure, cirrhosis, hepatic encephalopathy, hepatorenal syndrome, hepatopulmonary syndrome, cirrhotic cardiomyopathy, hemodialysis-related hypotension, cardiogenic shock, ischemia-reperfusion injury, hypoxia, and trauma. In some methods, the cobinamide is administered at a dose of 1 to 500 mg. In some such aspects, the method further comprises administering a pharmaceutically effective amount of cobalamin or a biologically active derivative or analog thereof.

In one aspect, the invention provides a method for alleviating the symptoms of a disease state in a subject caused or exacerbated by the presence of excess nitric oxide (NO) in the subject comprising administering a pharmaceutically effective amount of cobinamide, wherein the subject is diagnosed as suffering from or at risk of developing a disease state caused or exacerbated by the presence of excess NO. In some methods, the disease state is sepsis, chronic liver failure, cirrhosis, hepatic encephalopathy, hepatorenal syndrome, hepatopulmonary syndrome, cirrhotic cardiomyopathy, hemodialysis-related hypotension, cardiogenic shock, ischemia-reperfusion injury, hypoxia, and trauma. In some such methods, the cobinamide is administered at a dose of 1 to 500 mg.

In another aspect, the invention provides a method for treating sepsis in a subject comprising administering a pharmaceutically effective amount of cobinamide to the subject. In some methods, the cobinamide is administered at a dose of 1 to 500 mg. In some such aspects, the method further comprises administering a pharmaceutically effective amount of cobalamin or a biologically active derivative or analog thereof.

In another aspect, the invention provides a method for treating a disease state in a subject caused or exacerbated by the presence of excess cyanide in the subject comprising: administering a pharmaceutically effective amount of cobinamide, or a derivative or analog thereof, to the subject. In some methods, the subject is a cigarette smoker or hemodialysis patient. In other aspects, the disease state is cystic fibrosis. In some methods, the excess cyanide is brought about by weapons of mass destruction. In other aspects, the cobinamide is administered at a dose of 1 to 500 mg. In some such methods, the method further comprises administering a pharmaceutically effective amount of cobalamin or a biologically active derivative or analog thereof.

In another aspect, the invention provides a method for alleviating the symptoms of a disease state in a subject caused or exacerbated by the presence of excess cyanide in the subject comprising administering a pharmaceutically effective amount of cobinamide, wherein the subject is diagnosed as suffering from or at risk of developing a disease state caused or exacerbated by the presence of excess cyanide. In some methods, the subject is a cigarette smoker or hemodialysis patient. In other methods, the disease state is cystic fibrosis. In some methods, the excess cyanide is brought about by weapons of mass destruction. In other methods, the cobinamide is administered at a dose of 100 mg to 1 g. In some aspects, the method further comprises administering a pharmaceutically effective amount of cobalamin or a biologically active derivative or analog thereof.

In another aspect, the invention provides a method for treating cyanide toxicity in a subject comprising administering a pharmaceutically effective amount of cobinamide to the subject. In some methods, the cobinamide is administered at a dose of 100 mg to 1 g. In some aspects, the method further comprises administering a pharmaceutically effective amount of cobalamin or a biologically active derivative or analog thereof.

In another aspect, the invention provides a method for treating smoke inhalation in a subject comprising administering a pharmaceutically effective amount of cobinamide to the subject. In some methods, the cobinamide is administered at a dose of 500 mg to 5 g. In some aspects, the method further comprises administering a pharmaceutically effective amount of cobalamin or a biologically active derivative or analog thereof.

In another aspect, the invention provides a method for treating side effects associated with administration of nitroprusside to a mammalian subject comprising: administering a pharmaceutically effective amount of cobinamide to the subject. In some methods, the cobinamide is administered at a dose of 100 mg to 1 g. In some aspects, the method further comprises administering a pharmaceutically effective amount of cobalamin or a biologically active derivative or analog thereof.

In another aspect, the invention provides pharmaceutical compositions comprising cobinamide and a pharmaceutically acceptable carrier. In some aspects, the pharmaceutical composition further comprises cobalamin and a pharmaceutically acceptable carrier. In other aspects, the pharmaceutical composition further comprises cobalamin, or a biologically active derivative or analog thereof, and a pharmaceutically acceptable carrier.

In another aspect, the invention provides a pharmaceutical composition comprising one or more cobinamide compound(s), or a biologically active derivative(s) or analog(s) thereof, formulated for delivery to a subject, wherein the composition is effective for treating a disease state in a subject caused or exacerbated by the presence of excess nitric oxide (NO) in the subject. In some aspects, the pharmaceutical composition further comprises cobalamin, or a biologically active derivative or analog thereof, formulated for delivery.

In another aspect, the invention provides a pharmaceutical composition comprising one or more cobinamide compound(s), or a biologically active derivative(s) or analog(s) thereof, formulated for delivery to a subject, wherein the composition is effective to alleviate one or more symptom(s) of a disease state in a subject caused or exacerbated by the presence of excess nitric oxide (NO) in the subject. In some aspects, the pharmaceutical composition further comprises cobalamin, or a biologically active derivative or analog thereof, formulated for delivery.

In another aspect the invention provides a pharmaceutical composition comprising one or more cobinamide compound(s), or a biologically active derivative(s) or analog(s) thereof, formulated for delivery to a subject, wherein the composition is effective for treating a disease state in a subject caused or exacerbated by the presence of excess cyanide in the subject. In some aspects, the pharmaceutical composition further comprises cobalamin, or a biologically active derivative or analog thereof, formulated for delivery.

In another aspect, the invention provides a pharmaceutical composition comprising one or more combinamide compound(s), or a biologically active derivative(s) or analog(s) thereof, formulated for delivery to a subject wherein the composition is effective to alleviate one or more symptom(s) of a disease state in a subject caused or exacerbated by the presence of excess cyanide in the subject. In some aspects, the pharmaceutical composition further comprises cobalamin, or a biologically active derivative or analog thereof, formulated for delivery.

DETAILED DESCRIPTION

1. Introduction

Figure 1:
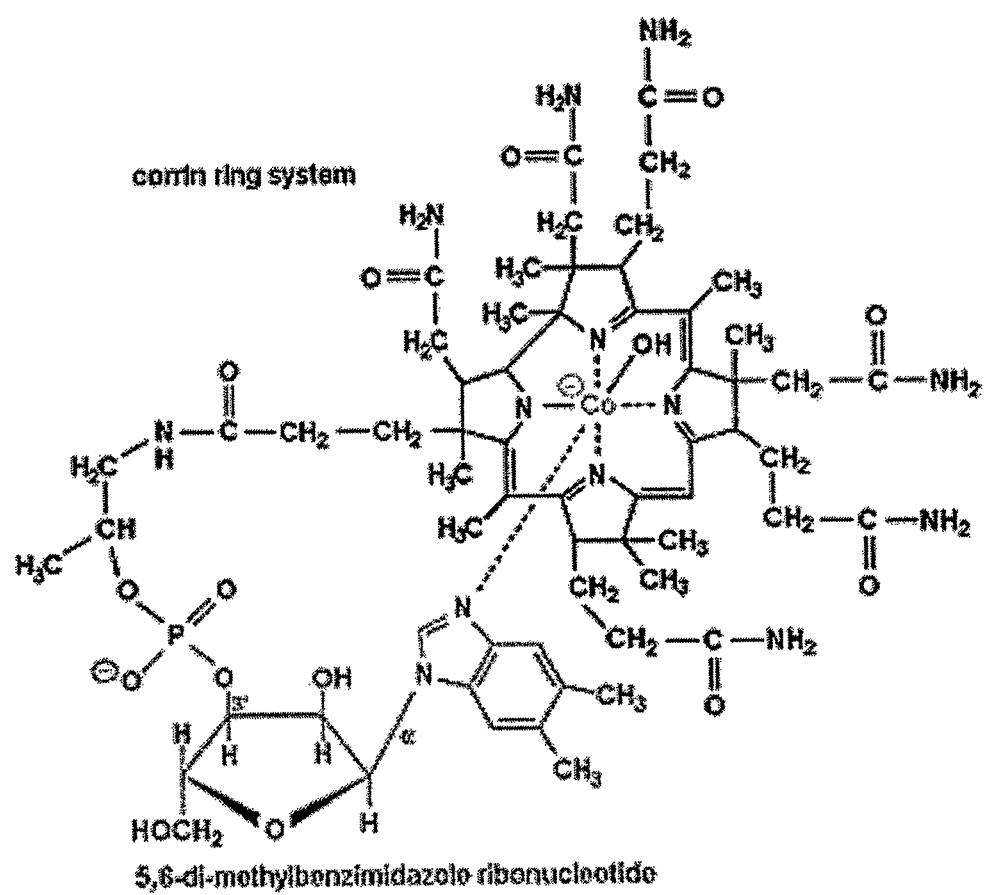
FIG. 1. Structure of Cobinamide and Cobalamin. The structure of cobalamin is shown. Cobinamide lacks the 5,6-dimethylbenzimidazole ribonucleotide tail shown in grey.

The invention provides a number of methods, reagents, and compositions that can be used for the treatment of disease states in a subject caused or exacerbated by the presence of excess nitrous oxide (NO) or excess cyanide in a subject.

It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The compounds employed in the methods of the present invention can be prepared in a number of ways well known to those skilled in the art. Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention. All processes disclosed in association with the present invention are contemplated to be practiced on any scale, including milligram, gram, multigram, kilogram, multikilogram or commercial industrial scale.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Some abbreviations used herein include: BHK, baby hamster kidney cells; CoA, coenzyme A; Deta-NONOate, (Z)-1-[2-(2-aminoethyl)-N-(2-ammonioethyl)amino]diazen-1-ium-1,2-diolate; DME, Dulbecco's Modified Eagle's medium; FBS, fetal bovine serum; G-kinase, cGMP-dependent protein kinase; HPLC, high performance liquid chromatography; LPS, lipopolysaccharide; NO, nitric oxide; NOS, NO synthase; OH-Cbl, hydroxocobalamin; PAPA-NONOate, (Z)-1-[N-(3-ammoniopropyl)-N-(n-propyl)amino]diazen-1-ium-1,2-diolate; PBS, phosphate-buffered saline; 8-pCPT-cGMP, 8-para-chlorophenylthio-cyclic GMP; and VASP, vasodilator-stimulated phosphoprotein.

"Sepsis" or "septic shock" refers to a spectrum of clinical conditions caused by the immune response of a host to infection or trauma and characterized by systemic inflammation and coagulation. It ranges from a systemic inflammatory response to organ dysfunction to multiple organ failure, and ultimately death for many patients. Particularly in elderly, immunocompromised, and critically ill patients, sepsis is a major cause of morbidity and mortality in intensive care units (ICUs) worldwide. In the US, sepsis is the leading cause of death in noncoronary ICU patients, while recent 1998 data from the Centers for Disease Control (CDC) show that it is the 11th leading cause of death overall (National Vital Statistics Report, 2000). Sepsis has been associated with mortality rates ranging from 28% to 50%.

"Hepatic encephalopathy" describes a condition which is used to describe the deleterious effects of liver failure on the central nervous system. Features include confusion ranging to unresponsiveness (coma). A common cause of hepatic encephalopathy is alcoholic cirrhosis.

"Hepatorenal syndrome" describes a condition in which acute renal failure occurs with disease of the liver or biliary tract, the cause of which is believed to be either a decrease in renal blood flow or damage to both the liver and the kidneys as from carbon tetrachloride poisoning or leptospirosis. Hepatorenal syndrome is also referred to as hepatonephric syndrome.

"Hepatopulmonary syndrome" describes a syndrome occurring in patients with chronic liver diseases, where the typical findings are vascular dilations in the lungs and impaired oxygenation. Dyspnea can be a common symptom, nail clubbing and cyanosis being the common findings.

"Cirrhotic cardiomyopathy" is generally defined as subnornal ventricular response to stress in the face of high resting cardiac output. Mechanistic studies in experimental animal models of cirrhosis indicate that multiple factors are responsible, including abnormal biophysical membrane characteristics, impaired β-adrenergic signal transduction and increased activity of cardiodepressant systems mediated by cGMP. Cirrhotic cardiomyopathy appears to be precipitated or worsened by liver transplantation, insertion of transjugular intrahepatic portosystemic stent-shunts and infection. It can play a role in the pathogenesis of hepatorenal syndrome.

"Hemodialysis-induced hypotension" refers to one of the most serious complications in renal replacement therapy. The main cause of intradialytic hypotension is hypovolemia due to an imbalance between the amount of fluid removed and the refilling capacity of the intravascular compartment. Hypotension occurs when compensatory mechanisms for hypovolemia are overwhelmed by excessive fluid removal. As long as renal replacement therapy is limited to only a few hours per week, intradialytic hypotension will continue to be a relevant problem. "Hypotension" refers to a condition where arterial pressure (MAP)<70 mm Hg; systolic blood pressure (SBP) <100 mm. Hg was used as a secondary outcome.

"Cardiogenic shock" refers to shock resulting from primary failure of the heart in its pumping function, as in myocardial infarction, severe cardiomyopathy, or mechanical obstruction or compression of the heart; clinical characteristics are similar to those of hypovolemic shock.

"Ischemia-reperfusion injury" refers to injury occurring during the restoration of blood flow to a tissue under low oxygen state.

"Hypoxia" refers to a condition in which there is a decrease in the oxygen supply to a tissue.

"Trauma" medically refers to a serious or critical bodily injury, wound, or shock.

"Cyanide toxicity" refers to cyanide as a source of poisoning. Cyanide exposure occurs relatively frequently in patients with smoke inhalation from residential or industrial fires.

Cyanide poisoning also can occur in industry, particularly in the metal trades, mining, electroplating, jewelry manufacture, and x-ray film recovery. It is also encountered in the fumigation of ships, warehouses, and other structures. Cyanides are used as suicidal agents, particularly among health care and laboratory workers. Numerous forms of cyanide exist, including gaseous hydrogen cyanide (HCN), water-soluble potassium and sodium cyanide salts, and poorly water-soluble mercury, copper, gold, and silver cyanide salts. In addition, a number of cyanide-containing compounds, known as cyanogens, can release cyanide during metabolism. These include, but are not limited to, cyanogen chloride and bromide (gases with potent pulmonary irritant effects), nitriles (R—CN), and sodium nitroprusside, which can produce cyanide poisoning during prolonged or high-dose therapy. Industry widely employs nitriles as solvents and in the manufacturing of plastics. Nitriles can release HCN during burning or when metabolized following absorption by the skin or gastrointestinal tract. A number of synthesized (e.g., polyacrylonitrile, polyurethane, polyamide, urea-formaldehyde, melamine) and natural (e.g., wool, silk) compounds produce HCN when burned. These combustion gases likely contribute to the morbidity and mortality of smoke inhalation. Finally, chronic consumption of cyanide-containing foods, such as cassava, can lead to cyanide poisoning. Depending on its form, cyanide can cause toxicity through inhalation, ingestion, or dermal absorption.

Cyanide affects virtually all body tissues, attaching itself to ubiquitous metalloenzymes and rendering them inactive. Its principal toxicity probably results from inactivation of cytochrome oxidase (cytochrome $aa_3$) and, thus, cellular respiration, even in the presence of adequate oxygen stores. Consequently, the tissues with the highest oxygen requirements (e.g., brain, heart, liver) are the most profoundly affected by acute cyanide poisoning.

Chronic consumption of cyanide-containing foods results in ataxia and optic neuropathy. Defective cyanide metabolism causes Leber optic atrophy, leading to blindness. Cyanide can cause some of the adverse effects associated with chronic smoking, such as tobacco amblyopia.

"Carbon monoxide (CO) toxicity" refers to toxicity from carbon monoxide (CO) formed as a by-product of burning organic compounds. Stoves, portable heaters, and automobile exhaust with malfunctioning or obstructed exhaust systems can cause CO toxicity. Cigarette smoke is a significant source of CO. Natural gas contains no CO, but improperly vented gas water heaters, kerosene space heaters, charcoal grills, hibachis, and Sterno stoves all emit CO. CO intoxication also occurs by inhalation of methylene chloride vapors, a volatile liquid found in degreasers, solvents, and paint removers. Dermal methylene chloride exposure can not result in significant systemic effects but can cause significant dermal burns. Liver metabolizes as much as one third of inhaled methylene chloride to CO. A significant percentage of methylene chloride is stored in the tissues, and continued release results in elevated CO levels for at least twice as long as with direct CO inhalation.

"Hemodialysis" refers to a type of kidney dialysis (most frequently used for patients who have kidney failure but can also be used to quickly remove drugs or poisons in acute situations) Hemodialysis works by circulating the blood through special filters. The blood flows across a semi-permeable membrane (the dialyzer or filter), along with solutions that help remove toxins from the blood. Hemodialysis generally requires a blood flow of 400 to 500 milliliters per minute (ml/min).

"Cystic fibrosis" refers to a hereditary disease of the exocrine glands, usually developing during early childhood and affecting mainly the pancreas, respiratory system, and sweat glands. It is characterized by the production of abnormally viscous mucus by the affected glands, usually resulting in chronic respiratory infections and impaired pancreatic function. Cystic fibrosis is also called mucoviscidosis.

"Renal failure" refers to when the kidneys fail to function properly. It can broadly be divided into two categories—acute renal failure and chronic renal failure. "Acute renal failure" is a rapidly progressive loss of renal function, generally characterized by oliguria (decreased urine production, quantified as less than 400-500 mL/day in adults, less than 0.5 mL/kg/hr in children or less than 1 mL/kg/hr in infants), body fluid disturbances and electrolyte derangement. An underlying cause must be identified to arrest the progress, and dialysis can be necessary to bridge the time gap required for treating these underlying causes. Chronic renal failure develops slowly and gives few symptoms initially. It can be the complication of a large number of kidney diseases, such as IgA nephritis, glomerulonephritis, chronic pyelonephritis and urinary retention. End-stage renal failure (ESRF) is the ultimate consequence, in which case dialysis is generally required while a donor for renal transplant is found. Chronic renal failure can be caused by a number of disorders which include long-standing hypertension, diabetes, congestive heart failure, lupus or sickle cell anemia. Chronic renal failure can be triggered by a number of acute disease processes. Examples include sepsis (infection), shock, trauma, kidney stones, kidney infection, drug toxicity (aspirin or lithium), poisons or toxins (drug abuse) or after injection with an iodinated contrast dye (adverse effect). Both forms of renal failure result in a life-threatening metabolic derangement.

"Weapons of mass destruction" or "WMD" are weapons designed to kill large numbers of people, typically targeting civilians and military personnel alike. http://encyclopedia.laborlawtalk.com/Weapons_of_mass_destruction.

Some types of WMDs are considered to have a psychological impact rather than a strictly military usefulness. Though the phrase was coined in 1937 to describe aerial bombardment by conventional explosive bombs in large quantities, the types of weapons today considered to be in this class are often referred to as NBC weapons or ABC weapons: Nuclear weapons (including radiological weapons), Biological weapons, Chemical weapons, and Explosive material. WMDs are also known as weapons of indiscriminate destruction, weapons of mass disruption and weapons of mass effects.

The modern military definition is "Weapons that are capable of a high order of destruction and/or of being used in such a manner as to destroy large numbers of people. Weapons of mass destruction can be high explosives or nuclear, biological, chemical, and radiological weapons, but exclude the means of transporting or propelling the weapon where such means is a separable and divisible part of the weapon." (source, Joint Publication 1-02, http://www.dtic.mil/doctrine/jel/new_pubs/ip1_02.pdf). An example of a chemical WMD includes, but is not limited to, cyanide poisoning.

As used in U.S. civil defense activities the definition is much broader. This category now includes the CBRNE weapons—Chemical, Biological, Radiological, Nuclear, and Explosive. In this listing a "Weapon of Mass Destruction" has been defined as, "(1) Any explosive, incendiary, poison gas, bomb, grenade, or rocket having a propellant charge of more than four ounces, missile having an explosive or incendiary charge of more than one-quarter ounce, or mine or device similar to the above. (2) Poison gas. (3) Any weapon involving a disease organism. (4) Any weapon that is designed to release radiation at a level dangerous to human life." 18 U.S.C. §2332a.

"Derivative" refers to a compound that is produced from another compound of similar structure by the replacement of substitution of one atom, molecule or group by another. For example, a hydrogen atom of a compound can be substituted by alkyl, acyl, amino, and the like, to produce a derivative of that compound.

The term "stable", as used herein, refers to compounds which possess the ability to allow manufacture and which maintain their integrity for a sufficient period of time to be useful for the purposes detailed herein. Typically, the compounds of the present disclosure are stable at a temperature of 40° C. or less in the absence of moisture or other chemically reactive conditions for at least a week.

"Patient", "subject", or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative or palliative treatment.

The term "administering," as used herein, means either directly administering a compound or composition of the present invention, or administering a prodrug, derivative or analog which will form an equivalent amount of the active compound or substance within the body. The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., C1-6 alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Pharmaceutically acceptable carrier (or medium)", which can be used interchangeably with "biologically compatible carrier or medium", refers to reagents, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds). As used herein, the term biodegradable describes the ability of a material to be broken down (e.g., degraded, eroded, dissolved) in vivo. The term includes degradation in vivo with or without elimination (e.g., by resorption) from the body. The semi-solid and solid materials can be designed to resist degradation within the body (non-biodegradable) or they can be designed to degrade within the body (biodegradable, bioerodable). A biodegradable material can further be bioresorbable or bioabsorbable, i.e., it can be dissolved and absorbed into bodily fluids (water-soluble implants are one example), or degraded and ultimately eliminated from the body, either by conversion into other materials or breakdown and elimination through natural pathways.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention can exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount", "effective amount" and grammatical variations thereof, as they refer to pharmaceutical compositions of the invention, are used interchangeably and represent the amount that, when administered to a subject for treating a disease or condition, is sufficient to effect treatment for that disease or condition. "Therapeutically effective amount," as used herein, refers to an amount effective, at dosages, and for periods of time necessary, to achieve the desired result. In particular, "therapeutically effective amount" refers to the amount of compound or composition of compounds that would treat a disease state in a subject caused or exacerbated by the present of excess nitric oxide or cyanide toxicity in a subject.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens can be adjusted to provide the improved therapeutic response. A therapeutically effective amount is also one in which any toxic or detrimental effects of the components are outweighed by the therapeutically beneficial effects.

"Concomitant administration" of a known therapeutic drug with a pharmaceutical composition of the present invention means administration of the drug and composition comprising cobinamide, or biologically active derivative or analog thereof, at such time that both the known drug and the composition will have a therapeutic effect. Such concomitant administration can involve concurrent (i.e. at the same time), prior, or subsequent administration of the antimicrobial drug with respect to the administration of a compound of the present invention. A person of ordinary skill in the art, would have no difficulty determining the appropriate timing, sequence and dosages of administration for particular drugs and compositions of the present invention.

The term "combination therapy" refers to the administration of two or more therapeutic agents or compounds to treat a therapeutic condition or disorder described in the present disclosure, for example, sepsis, chronic liver failure, cirrhosis, hepatic encephalopathy, hepatorenal syndrome, hepatopulmonary syndrome, cirrhotic cardiomyopathy, hemodialysis-related hypotension, cardiogenic shock, ischemia-reperfusion injury, hypoxia, or trauma. Other therapeutic conditions or disorders described in the present disclosure include, for example, cyanide toxicity. Such administration includes co-administration of these therapeutic agents or compounds in a simultaneous manner, such as in a single compound having cobinamide activity or in multiple, separate compounds for each cobinamide and cobalamin activities (including separate compounds administered in a single dosage unit). In addition, such administration also includes use of each type of therapeutic agent in a concurrent manner. In either case, the treatment regimen will provide beneficial effects of the drug combination in treating the conditions or disorders described herein.

In general, the phrase "well tolerated" refers to the absence of adverse changes in health status that occur as a result of the treatment and would affect treatment decisions.

"Synergistic interaction" refers to an interaction in which the combined effect of two or more agents is greater than the algebraic sum of their individual effects.

"Chronic" administration refers to administration of the agent(s) in a continuous mode as opposed to an acute mode, so as to maintain the initial therapeutic effect (activity) for an extended period of time. "Intermittent" administration is treatment that is not consecutive without interruption, but rather is cyclic in nature.

As used herein, "dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms of the invention can be dictated by (a) the unique characteristics of the active compound(s) and the particular therapeutic effect (s) to be achieved, and (b) the limitations inherent in the art of compounding such active compound(s).

The terms "component", "drug", "biologically active agent", "pharmacologically active agent", "active agent" or "medicament" are used interchangeably herein to refer to a compound or compounds or composition of matter which, when administered to an organism (human or animal) induces a desired pharmacologic and/or physiologic effect by local and/or systemic action.

The term "modulation" refers to the capacity to either enhance or inhibit a functional property of a biological activity or process, for example, receptor binding or signaling activity. Such enhancement or inhibition can be contingent on the occurrence of a specific event, such as activation of a signal transduction pathway and/or can be manifest only in particular cell types. The modulator is intended to comprise any compound, e.g., antibody, small molecule, peptide, oligopeptide, polypeptide, or protein, preferably small molecule, or peptide.

As used herein, "prodrug" refers to compounds specifically designed to maximize the amount of active species that reaches the desired site of reaction that are of themselves typically inactive or minimally active for the activity desired, but through biotransformation are converted into biologically active metabolites. Various forms of prodrugs are known in the art, for example, as discussed in Bundgaard, (ed.), DESIGN OF PRODRUGS, Elsevier, 1985; Widder et al. (ed.), METHODS IN ENZYMOLOGY, Vol. 4, Academic Press, 1985; Krogsgaard-Larsen et al., (ed). "Design and Application of Prodrugs," TEXTBOOK OF DRUG DESIGN AND DEVELOPMENT, Chapter 5: 113-191, 1991, Bundgaard et al, *Journal of Drug Deliver Reviews* 8: 1-38, 1992, Bundgaard, *J. of Pharmaceutical Sciences* 77: 285, 1988.; and Higuchi and Stella (eds.) PRODRUGS AS NOVEL DRUG DELIVERY SYSTEMS, American Chemical Society, 1975.

The compounds employed in the methods of the present invention can exist in prodrug form. As used herein, "prodrug" is intended to include any covalently bonded carriers that release the active parent drug, or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, and the like) the compounds employed in the present methods can, if desired, be delivered in prodrug form. Thus, the present invention contemplates methods of delivering prodrugs. Prodrugs of the compounds employed in the present invention, for example cobinamide, can be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

2. Overview

A. Nitric Oxide (NO) Scavenging and Cobinamide

Nitric oxide (NO) has multiple cellular functions including regulation of cell growth, differentiation, and apoptosis, and many physiological roles including modulation of blood pressure, platelet aggregation, and synaptic plasticity (Lloyd-Jones and Bloch, *Annu. Rev. Med.* 47: 365-375, 1996; Ignarro, L. and Murad, F. (1995) Nitric oxide. Biochemistry, molecular biology and therapeutic implications, Academic Press, San Diego; Hölsher, *Trends Neurosci.* 20: 298-303, 1997). Studies of NO's functions have been aided by pharmacologic agents that raise or lower NO levels (Moncada et al., *Pharmacol. Rev.* 43: 109-142, 1991). A number of disease states including sepsis and hepatic failure are characterized by abnormally high NO production, and removing the excess NO could have salutary effects (Shah et al., *Gastroenterology* 126: 903-913, 2004; Komeno et al., *J. Vet. Med. Sci.* 66: 53-57, 2004; Pfeilschifter et al., *Pflugers Arch.* 442: 479-486, 2001).

One approach to lower NO concentrations is to reduce NO synthesis. Four NO synthase (NOS) isoforms are present in mammals: neuronal NOS (nNOS or NOS I), inducible NOS (iNOS or NOS II), endothelial NOS (eNOS or NOS III), and a recently described mitochondrial NOS (mtNOS) (Nedvetsky et al., *Proc. Natl. Acad. Sci. U.S.A* 99: 16510-16512, 2002; Elfering et al., *J. Biol. Chem.* 277: 38079-38086, 2002). nNOS and eNOS are constitutively expressed in many tissues, and produce pico to nanomolar concentrations of NO in response to increased intracellular calcium (Clancy and Abramson, *Proc. Soc. Exp. Biol. Med.* 210: 93-101, 1995). iNOS is expressed in a variety of cell types, and its level can be induced many-fold by endotoxin (lipopolysaccharide, LPS) and tumor necrosis factor-alpha, with iNOS producing almost 1000 times higher NO—i.e., nano to micromolar—concentrations than nNOS and eNOS (Pfeilschifter et al., *Pflugers Arch* 442: 479-486, 2001 Poon et al., *Circulation* 108: 1107-1112, 2003; Morin et al., *Crit. Care Med.* 26: 1258-1264, 1998; Nathan, *FASEB J.* 6: 3051-3064, 1992). Less is known about mtNOS, but it accounts for 50% of cellular NO production in rat liver, and low micromolar NO concentrations have been found in rat heart mitochondria (Elfering et al., *J. Biol. Chem.* 277: 38079-38086, 2002; Saavedra-Molina et al., *Amino Acids* 24: 95-102, 2003). A large number of NOS inhibitors have been generated, most of which are arginine analogs including isothiourea derivatives, and because of arginine's multiple biochemical roles, these agents can have affects other than NOS inhibition (Garvey et al., *J. Biol. Chem.* 269: 26669-26676, 1994; El Mabrouk et al., *Life Sci.* 67: 1613-1623, 2000; Hallemeesch et al., *Clin. Nutr.* 21: 111-117, 2002).

Another approach to reduce NO levels is to use an NO scavenger. For example, the heme moiety of hemoglobin binds NO with great avidity, but heme and free extracellular hemoglobin can be highly toxic, particularly in whole animals (Kim and Greenburg, *Shock* 17: 423-426, 2002). Thus, other NO scavengers have been considered including dithiocarbamate derivatives that chelate iron and thus bind NO, but these too can have adverse effects (Menezes et al., *Am. J. Physiol.* 277: G144-G151, 1999; Nadler et al., *Am. J. Physiol.* 281: G173-G181, 2001). Cobalamin (vitamin $B_{12}$) is structurally similar to heme, and also binds NO, but with considerably less efficiency than heme (Greenberg et al., *J. Pharmacol. Exp. Ther.* 273: 257-265, 1995). The cobalamin precursor cobinamide, which lacks the dimethylbenzimidazole ribonucleotide tail of cobalamin (FIG. 1), has a more than 100 times greater affinity for NO than cobalamin; moreover, each cobinamide molecule can potentially neutralize two NO molecules, compared to only one NO molecule for cobalamin (Sharma et al., *Biochemistry* 42: 8900-8908, 2003). As disclosed herein, studies demonstrating cobinamide's use as an NO scavenger, both in a *Drosophila* model and in cultured mammalian cells are presented. Cobinamide became toxic to cells at concentrations considerably higher than would be needed to neutralize NO produced in vivo, and the toxicity was reversed fully by cobalamin; cobalamin did not affect NO scavenging by cobinamide, and thus the combination of these two corrinoids can be a very effective method to scavenge NO.

B. Cyanide Toxicity and Cobinamide

Cyanide is a potent toxin with the $LD_{50}$ of KCN for animals in the range of 2-8 mg/kg, and in humans as little as 50 mg can be fatal (Salkowski and Penney, *Vet. Hum. Toxicol.* 36: 455-466, 1994). It has been used throughout history as a homicidal and suicidal agent, and was used in chemical warfare in World War I, in mass poisonings of Jews by the Nazis (referred to as Zyklon B) in World War II, and likely during the Iran-Iraq War in the early 1980's (Way, *Annu. Rev. Pharmacol. Toxicol.* 24: 451-481, 1984; 2004. Fact Sheet, CDC. Dept. Health and Human Services). Cyanide has the potential to be used as a weapon of mass destruction, particularly in closed spaces such as airports and train stations (Greenfield et al., *Am. J. Med. Sci.* 323: 326-340, 2002; Rotenberg, *Pediatr. Ann.* 32: 236-240, 2003; Eckstein, *JEMS* 29: suppl-31, 2004).

Cyanide gas is generated during the combustion of any material containing carbon and nitrogen including cotton, plastics, silk, and wool, and thus, it is produced in residential and industrial fires (Alcorta, *JEMS* 29: suppl-15, 2004). With the advent of more synthetic-based materials used in construction, cyanide gas can be responsible for as many deaths from smoke inhalation as carbon monoxide (Alcorta, *JEMS* 29: suppl-15, 2004; Alarie, *Crit. Rev. Toxicol.* 32: 259-289, 2002; Esposito and Alarie, *J. Fire Sci.* 6: 195-242, 1988; Silverman et al., *J. Trauma* 28: 171-176, 1988). Cyanide binds to metalloenzymes, and its primary intracellular target is considered to be cytochrome oxidase, thus uncoupling oxidative phosphorylation and depleting cells of ATP.

There are several antidotes for cyanide intoxication including sodium nitrite, sodium thiosulfate, and hydroxo-cobalamin (vitamin $B_{12b}$) (Gracia and Shepherd, *Pharmacotherapy* 24: 1358-1365, 2004; Cummings, *Occup. Med. (Lond)* 54: 82-85, 2004; Megarbane et al., *J. Chin Med. Assoc.* 66: 193-203.). Sodium nitrite acts by generating methhemoglobin (ferric hemoglobin), which has a high affinity for cyanide but can no longer bind oxygen, and thus in smoke inhalation victims sodium nitrite can exacerbate the reduction in oxygen-carrying capacity induced by carbon monoxide (Moore et al., *J. Pharmacol. Exp. Ther.* 242: 70-73, 1987). Sodium thiosulfate acts as a sulfur donor for the enzyme rhodanese, which converts cyanide to thiocyanate, a non-toxic cyanide derivative. Hydroxo-cobalamin acts by binding cyanide with a relatively high affinity ($K_A$ of approximately $10^{12}$), and because of its high stability, cyano-cobalamin is the common form of cobalamin in vitamin preparations. In the United States, sodium nitrite and sodium thiosulfate are used as cyanide antidotes, while in France and several other European countries hydroxo-cobalamin is favored (Fortin et al., *JEMS* 29: suppl-21, 2004).

Cobinamide is the penultimate precursor in the biosynthesis of cobalamin, lacking the dimethylbenzimidazole (DBZ) nucleotide tail of cobalamin. The DBZ group is coordinated to the cobalt atom in the lower axial position, and thus, whereas cobalamin has only one upper ligand binding site, cobinamide has both an upper and lower ligand binding site. Moreover, in cobalamin, the DBZ group has a negative trans effect on the upper binding site, thereby reducing the binding affinity of cobalamin for ligands. The net effect is that cobinamide has a much greater affinity for cyanide ion than cobalamin, with a $K_A$ of approximately $10^{22}$. As disclosed herein using two different biological systems, cobinamide more effectively detoxifies cyanide than cobalamin, and, as previously shown, clinically-relevant concentrations of cobinamide are non-toxic to mammalian cells (Broderick et al., *J. Biol. Chem.* 280: 8678-8685, 2005). Thus, cobinamide can be useful as an antidote for cyanide poisoning.

3. Disease Indications

A. Nitric Oxide Disease States

The methods of the present invention are directed to treating and preventing disease states in a subject caused or exacerbated by the presence of excess nitric oxide (NO) in the subject comprising administering a pharmaceutically effective amount of cobinamide, or a biologically active derivative or analog thereof, to the subject.

The methods of the present invention are also directed to alleviating the symptoms of a disease state in a subject caused or exacerbated by the presence of excess nitric oxide (NO) in the subject comprising administering a pharmaceutically effective amount of cobinamide, wherein the subject is diagnosed as suffering from or at risk of developing a disease state caused or exacerbated by the presence of excess NO.

Septic shock is characterized by drug-refractory hypotension, and has an extremely high mortality rate. Various cytokines and signaling molecules contribute to the septic state, with nitric oxide (NO) playing a major role in the development of the severe hypotension. NO is produced by three different NO synthases: neuronal NOS (nNOS), inducible NOS (iNOS), and endothelial NOS (eNOS). A marked induction of iNOS is largely responsible for the increased NO levels in sepsis. Non-selective NOS inhibitors showed some success in animal models of sepsis, but in a large Phase III Clinical Trial, one of these agents resulted in increased mortality. Selective iNOS inhibitors have shown more promise in animal models, but have yet to be tried in humans.

Another approach to lower NO levels in sepsis is to use an NO scavenger, and several NO scavengers including hemoglobin and vitamin $B_{12}$ (cobalamin) have been shown to be beneficial in animal models of sepsis. As disclosed herein, cobinamide, which lacks the dimethyl-benzimidazole (DBZ) nucleotide tail of cobalamin, binds NO approximately 100 times more tightly than cobalamin, both in physiologic buffer and in human serum. In cultured mammalian cells and in a well-established *Drosophila* model as disclosed herein, that cobinamide is an effective NO scavenger, and exhibits no toxicity at the concentrations that would be required to scavenge NO in sepsis.

In addition to shock, several other clinical states are characterized by excess NO production. These include hepatic encephalopathy, hepatorenal syndrome, hepatopulmonary syndrome, cirrhotic cardiomyopathy, hemodialysis-related hypotension, cardiogenic shock, ischemia-reperfusion injury, hypoxia, and trauma (Pfeilschifter et al., *Pflugers Arch.* 442: 479-486, 2001; Shah et al., *Gastroenterology* 126: 903-913, 2004; Komeno et al., *J. Vet. Med. Sci.* 66: 53-57, 2004). In several of these conditions, the mechanism of increased NO is through a systemic inflammatory response with increased iNOS expression (Shah et al., *Gastroenterology* 126: 903-913, 2004; Hochman, *Circulation* 107: 2998-3002, 2003). Thus, an NO scavenger such as cobanimide can be useful in these conditions.

Therefore, in certain aspects, the methods of the invention are useful for the treatment and prevention of sepsis, chronic liver failure, cirrhosis, hepatic encephalopathy, hepatorenal syndrome, hepatopulmonary syndrome, cirrhotic cardiomyopathy, hemodialysis-related hypotension, cardiogenic shock, ischemia-reperfusion injury, hypoxia, and trauma.

B. Cyanide Toxicity

The methods of the present invention are directed to treating and preventing disease states in a subject caused or exacerbated by the presence of excess cyanide (i.e., cyanide toxicity) in the subject comprising administering a pharmaceutically effective amount of cobinamide, or a biologically active derivative or analog thereof, to the subject.

The methods of the present invention are also directed to alleviating the symptoms of a disease state in a subject caused or exacerbated by the presence of excess cyanide in the subject comprising administering a pharmaceutically effective amount of cobinamide, wherein the subject is diagnosed as suffering from or at risk of developing a disease state caused or exacerbated by the presence of excess cyanide Cyanide gas is generated during the combustion of any material containing carbon and nitrogen, and thus is generated during the burning of paper, wool, silk, and plastics (Alcorta, R. 2004).

Smoke Inhalation

Cyanide gas is generated during the combustion of any material containing carbon and nitrogen, and thus is generated during the burning of paper, wool, silk, and plastics. Most victims of fires die from smoke inhalation, and the two most toxic gases in smoke are cyanide and carbon monoxide (Alcorta, *JEMS* 29: suppl-15, 2004; Esposito and Alarie, *J. Fire Sci.* 6: 195-242, 1988; Alarie, *Crit. Rev. Toxicol.* 32: 259-289, 2002; Silverman et al., *J. Trauma* 28: 171-176, 1988). Most victims of fires die from smoke inhalation, and the two most toxic gases in smoke are cyanide and carbon monoxide (Alcorta, *JEMS* 29: suppl-15, 2004; Esposito and Alarie, *J. Fire Sci.* 6: 195-242, 1988; Alarie, *Crit. Rev. Toxicol.* 32: 259-289, 2002; Silverman et al., *J. Trauma* 28: 171-176). With the advent of the use of more synthetic-based materials in construction, cyanide has assumed increasing importance in deaths during residential and industrial fires.

Cigarette Smokers

Cyanide is produced from tobacco smoke, and it has been known for some time that cigarette smokers have high serum and urinary concentrations of thiocyanate (SCN—), the immediate catabolic product of cyanide (Michigami et al., *Analyst* 113: 389-392, 1988; Abou-Seif, *J. Biochem. Toxicol.* 11: 133-138, 1996). Indeed, serum and urinary thiocyanate levels have been used in clinical studies to distinguish smokers from non-smokers, and to assess the amount of cigarettes consumed by smokers. Thiocyanate is produced from cyanide by the enzyme rhodanese, which is in high concentrations in the liver and in the respiratory tract epithelium. Thiocyanate can be considered a pseudo-halide, and it is a very good substrate for peroxidases, specifically myeloperoxidase, eosinophil peroxidase, and lactoperoxidase (Zhang et al., *Blood* 99: 1802-1810, 2002; van Dalen and Kettle, *Biochem. J.* 358: 233-239, 2001; Scanlon et al., *Atherosclerosis* 121: 23-33, 1996; Exner et al., *Free Radic. Biol. Med.* 37: 146-155, 2004). In peroxidase reactions H2O2 is consumed and an oxygen atom is transferred to an acceptor; in the case of thiocyanate, hypothiocyanite (OSCN—) is formed. Hypothiocyanite is a relatively weak oxidizing agent, but in addition to hypothiocyanite, more potent oxidizing compounds appear to be produced in the reaction of thiocyanate and H2O2, specifically cyanate (OCN—), hypthiocyanonus acid (HOSCN), cyanosulphurous acid (HO2SCN), and cyanosulphuric acid (HO3SCN). Each of these compounds can oxidize low density lipoproteins (LDLs) in the blood; oxidized LDLs lead to the formation of fatty streaks and atheromas in arteries, and thus to atherosclerosis (Zhang et al., *Blood* 99: 1802-1810, 2002; van Dalen and Kettle, *Biochem. J.* 358: 233-239, 2001; Scanlon et al., *Atherosclerosis* 121: 23-33, 1996; Exner et al., *Free Radic. Biol. Med.* 37: 146-155, 2004). There is considerable epidemiological data to suggest that the increased atherosclerotic disease in smokers can be from their increased thiocyanate levels, and the production of hypothiocyanite and other oxidized thiocyanate derivatives can be the basis for the increased atherogenesis.

Chronic Renal Failure

Serum thiocyanate levels are also increased in patients in chronic renal failure, and in patients on hemodialysis (Hasuike et al., *Nephrol. Dial. Transplant.* 19: 1474-1479, 2004). Cyanide is present in some foods and can also be produced in the gut by cyanogenic bacteria. Presumably the basis for increased thiocyanate levels in renal failure is because of decreased urinary excretion in the face of normal rates of production from cyanide. For unclear reasons, thiocyanate appears to be removed poorly by hemodialysis. Like cigarette smokers, hemodialysis and renal failure patients have a marked increase in atherosclerotic cardiovascular disease, and the basis for this can be from increased thiocyanate levels through the mechanism described for cigarette smokers. Thus, by lowering cyanide levels, cobinamide could be useful in the treatment of smoke inhalation, and in reducing the risk for atherosclerosis in smokers, and renal failure patients.

In certain aspects, the methods of the invention are also useful for the treatment of hemodialysis patients. In other aspects, the methods of the invention are useful for the treatment of cystic fibrosis, and excess cyanide brought about by weapons of mass destruction.

4. Formulation and Administration of Pharmaceutical Compositions

The compounds employed in the methods of the present invention can be administered by any means that results in the contact of the active agents with the agents' site or site(s) of action in the body of a patient. The compounds can be administered by any conventional means available for use in conjunction with pharmaceuticals, either as individual therapeutic agents or in a combination of therapeutic agents. For example, they can be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in the latest edition of Remington's Pharmaceutical Science, Mack Publishing Company, Easton, Pa. ("Remington's"), the disclosure of which is incorporated by reference in its entirety.

Compounds of the present invention can be administered to a mammalian host in a variety of forms adapted to the chosen route of administration, e.g., orally. Other acceptable routes of administration are parenteral including intravenous; transepithelial including transdermal, transnasal, ophthalmic, sublingual and buccal; topical including ophthalmic, dermal, ocular, and rectal; nasal or pulmonary inhalation via insufflation or aerosol; and rectal systemic.

The active compound can be orally administered, for example, with an inert diluent or with an assimilable edible carrier, it can be enclosed in hard or soft shell gelatin capsules, it can be compressed into tablets, or it can be incorporated directly with the food of the diet. For oral therapeutic administration, the active compound can be incorporated with excipient and used in the form of ingestible tablets, buccal tablets, troches, capsules, elixirs, suspensions, syrups, wafers, and the like. The amount of active compound(s) in such therapeutically useful compositions is from about 10 mg/day to about 1000 mg/day of active compound.

In certain aspects of the invention, cobinamide, or biologically active derivative or analog thereof, stereoisomer, prodrug, pharmaceutically acceptable salt, hydrate, solvate, acid salt hydrate, N-oxide or isomorphic crystalline form thereof is administered at a level of at least about 10 mg/day, more preferably at a level of at least about 100 mg/day, even more preferably at a level of at least about 500 mg/day, and yet even more preferably at a level of at least about 1000 mg/day.

In certain aspects of the invention, cobinamide, or biologically active derivative or analog thereof, stereoisomer, prodrug, pharmaceutically acceptable salt, hydrate, solvate, acid salt hydrate, N-oxide or isomorphic crystalline form thereof is administered at a level of at a level of less than about 100 mg/day, more preferably at a level of less than about 500 mg/day, even more preferably at a level of less than about 1000 mg/day, and yet even more preferably at a level of less than about 2000 mg/day.

In accordance with the methods of the present invention, the cobinamide compounds can be administered to a patient in a dosage range of from about 1 mg/day to about 1000 mg/day (and all combinations and subcombinations of dosage ranges and specific dosages therein).

In certain aspects of the invention, cobinamide, or biologically active derivative or analog thereof, stereoisomer, prodrug, pharmaceutically acceptable salt, hydrate, solvate, acid salt hydrate, N-oxide or isomorphic crystalline form thereof is administered for at least about 1 day, more preferably for at least about 2 days, even more preferably for at least about 3 days, yet even more preferably, for at least about 5 days, and further more preferably, for at least about 7 days.

The tablets, troches, pills, capsules and the like can also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound can be incorporated into sustained-release preparations and formulations.

The compound(s) of the invention, or a biologically active derivative(s) or analog(s) thereof can also be administered in sustained delivery or sustained release mechanisms, which can deliver the formulation internally. For example, biodegradable microspheres or capsules or other biodegradeable polymer configurations capable of sustained delivery of a peptide can be included in the formulations of the invention. (See, e.g., Putney, *Nat. Biotechnol.* 16: 153-157, 1998).

The active compound can also be administered parenterally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations can contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms can be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be achieved by the use of agents delaying absorption, for example, aluminum monostearate and gelatin.

Sterile injectable solutions can be prepared by incorporating the active compounds in the required amounts, in the appropriate solvent, with various of the other ingredients enumerated above, as required, followed by filtered sterilization. Generally, dispersions can be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation can include vacuum drying and the freeze-drying technique that yield a powder of the active ingredient, plus any additional desired ingredient from the previously sterile-filtered solution thereof.

The therapeutic compounds of this invention can be administered to a patient alone or in combination with a pharmaceutically acceptable carrier. As noted above, the relative proportions of active ingredient and carrier can be determined, for example, by the solubility and chemical nature of the compounds, chosen route of administration and standard pharmaceutical practice.

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. (See, e.g., Sayani, *Crit. Rev. Ther. Drug Carrier Syst.* 13: 85-184, 1996.) For topical, transdermal administration, the agents are formulated into ointments, creams, salves, powders and gels. Transdermal delivery systems can also include, e.g., patches.

For inhalation, the compounds of the invention can be delivered using any system known in the art, including dry powder aerosols, liquid delivery systems, air jet nebulizers, propellant systems, and the like. See, e.g., Patton, *Biotechniques* 16: 141-143, 1998; product and inhalation delivery systems for polypeptide macromolecules by, e.g., Dura Pharmaceuticals (San Diego, Calif.), Aradigrn (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's.

The pharmaceutical compositions are generally formulated as sterile, substantially isotonic, and in full compliance with all Good Manufacturing Practice (GMP) regulations of the U.S. Food and Drug Administration.

5. Treatment Regimens and Pharmacokinetics

The pharmaceutical compositions of the invention can be administered in a variety of unit dosage forms depending upon the method of administration. Dosages are well known to those of skill in the art. Such dosages are typically advisorial in nature and are adjusted depending on the particular therapeutic context, patient tolerance, and the like. The amount of a compound of the invention adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer *Science* 249: 1527-1533, 1990.

In therapeutic applications, compositions are administered to a patient suffering from a disease state caused or exacerbated by the presence of excess nitric oxide (NO) or excess cyanide to at least partially arrest the condition or a disease and/or its complications. For example, in one aspect, a soluble pharmaceutical composition dosage for intravenous (IV) administration would be about 10 mg/hr to about 500 mg/hr administered over several hours (typically 1, 3, or 6 hours), which can be repeated for weeks with intermittent cycles. Considerably higher dosages (e.g., ranging up to about 1000 mg/hr) can be used, particularly when the drug is administered to a secluded site and not into the blood stream, such as into a body cavity or into a lumen of an organ, e.g., the cerebrospinal fluid (CSF) or a joint space or structure.

The invention provides pharmaceutical compositions comprising one or a combination of compounds, such as cobinamide and cobalamin, formulated together with a pharmaceutically acceptable carrier.

In prophylactic applications, pharmaceutical compositions or medicaments are administered to a patient susceptible to, or otherwise at risk of a disease or condition (e.g., caused by excess nitric oxide, sepsis, chronic liver failure, cirrhosis, hepatic encephalopathy, hepatorenal syndrome, hepatopulmonary syndrome, cirrhotic cardiomyopathy, hemodialysis-related hypotension, cardiogenic shock, ischemia-reperfusion injury, hypoxia, traumacyanide toxicity, caused by excess cyanide, the patient is a cigarette smoker, hemodialysis, cystic fibrosis, nitroprusside, or excess cyanide brought about by weapons of mass destruction) in an amount sufficient to eliminate or reduce the risk, lessen the severity, or delay the onset of the disease, including biochemical, histologic and/or behavioral symptoms of the disease, its complications, and intermediate pathological manifestations presenting during development of the disease. In therapeutic applications, compositions or medicants are administered to a patient suspected of, or already suffering from such a disease in an amount sufficient to cure, or at least partially arrest, the symptoms of the disease (biochemical, histologic, and/or behavioral), including its complications and intermediate pathological manifestations in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, any response is monitored and repeated dosages are given if the response starts to wane 6. Effective Dosages The dosage of the compounds of the present invention that will be most suitable for prophylaxis or treatment will vary with the form of administration, the particular compound chosen and the physiological characteristics of the particular patient under treatment. Generally, small dosages can be used initially and, if necessary, increased by small increments until the desired effect under the circumstances is reached. Generally speaking, oral administration can require higher dosages.

The combination products useful in the methods of this invention, such as pharmaceutical compositions comprising cobinamide, or a biologically active derivatives or analogs thereof, with additional active ingredients (e.g., cobalamin) can be in any dosage form, such as those described herein, and can also be administered in various ways, as described herein. In a preferred embodiment, the combination products of the invention are formulated together, in a single dosage form (that is, combined together in one capsule, tablet, powder, or liquid, and the like). When the combination products are not formulated together in a single dosage form, the cobinamide, or a biologically active derivatives or analogs thereof, and additional active ingredient (e.g., cobalamin) can be administered at the same time or simultaneously (that is, together), or in any order. When not administered at the same time or simultaneously, that is, when administered sequentially, preferably the administration of cobinamide, or a biologically active derivatives or analogs thereof, and additional active ingredient occurs less than about one hour apart, more preferably less than about 30 minutes apart, even more preferably less than about 15 minutes apart, and still more preferably less than about 5 minutes apart.

Preferably, administration of the combination products of the invention is oral, although other routes of administration, as described above, are contemplated to be within the scope of the present invention. Although it is preferable that the cobinamide, or a biologically active derivatives or analogs thereof, and the additional active ingredients are all administered in the same fashion (that is, for example, both orally), if desired, they can each be administered in different fashions (that is, for example, one component of the combination product can be administered orally, and another component can be administered intravenously). The dosage of the combination products of the invention can vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Particularly when provided as a single dosage form, the potential exists for a chemical interaction between the combined active ingredients. For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers can be present such that the placebo layer is between the layers of active ingredients. In addition, dosage forms of the present invention can be in the form of capsules wherein one active ingredient is compressed into a tablet or in the form of a plurality of microtablets, particles, granules or non-pareils, which are then enteric coated. These enteric coated microtablets, particles, granules or non-pareils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

7. Routes of Administration

Compositions for treating a disease state in a subject caused or exacerbated by the presence of excess nitric oxide (NO) or excess cyanide in the subject can be administered by parenteral, topical, intravenous, oral, subcutaneous, intraarterial, intracranial, intraperitoneal, intranasal, or intramuscular means as inhalants. Administration can also be subcutaneous. Other routes can be equally effective. Another common route of administration is intramuscular injection. This type of injection is most typically performed in the arm, shoulder, or leg muscles. In some methods, agents are injected directly into a particular tissue, for example intracranial injection or convection-enhanced delivery. Intramuscular injection or intravenous infusion are also contemplated. In some methods, the compositions of the invention are administered as a sustained release composition or device, such as a Medipad™ device.

8. Kits

Pharmaceutical kits useful in the methods of the invention are also within the ambit of the present invention. Sterilization of the container can be carried out using conventional sterilization methodology well known to those skilled in the art. The sterile containers of materials can comprise separate containers, or one or more multi-part containers, as exemplified by the UNIVIAL™ two-part container (available from Abbott Labs, Chicago, Ill.), as desired. The cobinamide, or biologically active derivative or analog thereof, and the optional additional active ingredient can be separate, or combined into a single dosage form as described above. Such kits can further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, can also be included in the kit.

Agents of the invention can optionally be administered in combination with other agents that are at least partly effective in treating disease and disorders as disclosed herein.

The invention provides for a pharmaceutical combinations, e.g., a kit, comprising a) a first agent which is a compound of the invention as disclosed herein, in free form or in pharmaceutically acceptable salt form, and b) at least one co-agent. The kit can comprise instructions for its administration.

Exemplary Embodiments

A. Nitric Oxide and Cobinamide

1. Materials and Methods

Production and Analysis of Cobinamide. Approximately 200 mg of hydroxo-cobalamin (OH-Cbl, Sigma Chemical Co.) was dissolved in 1 ml of concentrated HCl, and heated at 65° C. for 8 min to hydrolyze the phosphoester bond linking the dimethylbenzimidazole ribonucleotide moiety to the corrin ring [FIG. 1, (Hayward et al., *J. Chem. Soc.* 6485-6493, 1965)]. The solution was cooled on ice and applied to a 1 ml C18 solid phase extraction column (Fisher Scientific). The HCl and unreacted OH-Cbl were removed by batch elution in water and 10% acetone, respectively, and the diaquocobinamide (cobinamide) product was eluted in 20% acetone and concentrated under reduced pressure in a SpeedVac (Savant Industries). Purity of the cobinamide was confirmed both spectro-photometrically by comparison to published spectra (Sharma et al., *Biochemistry* 42: 8900-8908, 2003, Baldwin et al., *J. Chem. Soc. Dalton Trans.* 217-223, 1983, Ford et al., *J. Inorg. Biochem.* 41: 235-244, 1991), and by high performance liquid chromatography (HPLC) using a C18 reversed-phase column eluted isocratically in 100 mM $NaH_2PO_4$, pH 4.0/15% methanol (v/v) (Ford et al., *J. Inorg. Biochem.* 41: 235-244, 1991; Boss, *J. Biol. Chem.* 259: 2936-2941, 1984); the column effluent was monitored at multiple wavelengths by a diode array detector. The yield was generally >80% or approximately 160 mg of cobinamide was produced per batch. When stored at −20° C., the cobinamide was spectroscopically and biologically stable for at least one month.

Assessment of Malpighian Tubule Secretion in *Drosophila Melanogaster*. An elegant in vitro method has been devised to measure fluid transport by the Malpighian tubules of *D. melanogaster*; tubular secretion is stimulated markedly by NO donors and LPS, the latter via induction of the *Drosophila* NOS gene (Broderick et al., *Am. J. Physiol.* 285: C1207-C1218, 2003; Dow and Davies, *Physiol. Rev.* 83: 687-729, 2003). Briefly, two pairs of Malpighian tubules, each with a ureter, were dissected from ten wild type Oregon R adult flies anesthetized on ice. The tubules were mounted in liquid paraffin with the distal end of one tubule bathed in a 10 µl droplet of Schneider's Insect medium. Fluid secretion rates were determined at room temperature by measuring the size of drops formed at the end of the ureter every 10 min. Basal fluid secretion rates were measured for three 10 min intervals prior to adding 10 µM Deta-NONOate (Cayman Chemical Co.) or 1 µM LPS (Sigma Chemical Co.) to the droplet of Schneider's medium; after three more 10 min intervals, 10 µM cobinamide, with or without 10 µM OH-Cbl, was added to some of the tubules for a further 30 min. Each data point represents the mean from at least 20 pairs of tubules analyzed on three separate occasions. In some experiments, flies were grown for 48 h on food supplemented with 250 µM cobinamide prior to measuring rates of tubular secretion. The supplemented food was generated by liquifying standard fly food paste by heating to approximately 40° C., and after adding cobinamide, allowing the food to cool to room temperature. Malpighian tubules were dissected from the flies, and rates of tubular secretion were measured in the absence and presence of 1 µM LPS as described above.

Measurement of Cobinamide Uptake into Mammalian Cells. To study cobinamide uptake into mammalian cells, cobinamide was radioactively labeled with [$^{14}$C] by adding two molar equivalents of [$^{14}$C]-KCN (54 mCi/mmol, Moravek Biochemicals) to form [$^{14}$C]-dicyanocobinamide ([$^{57}$Co]-cobalamin is no longer commercially available). The binding affinity of cyanide for cobinamide is extremely high (K overall ~$10^{22}$ M$^{-1}$) (Pratt, J. M. (1972) Inorganic chemistry of vitamin B$_{12}$, Academic Press, London-New York), but to be sure no [$^{14}$C]-KCN remained, the pH was lowered to 6 to form HCN (pKa of KCN is 9.2), and then bubbled argon through the solution to remove any [$^{14}$C]-HCN. The specific activity of the [$^{14}$C]-dicyanocobinamide product was 104 mCi/mmol (using a molar extinction coefficient of $2.8 \times 10^4$ at 348 nm) (Ford et al., *J. Inorg. Biochem.* 41: 235-244, 1991).

In the uptake studies, approximately $1 \times 10^6$ baby hamster kidney (BHK) cells cultured in Dulbecco's Modified Eagles' (DME) medium containing 10% fetal bovine serum (FBS) were grown to sub-confluence in six well cluster dishes. The cells were incubated at 37° C. for 5 min with [$^{14}$C]-dicyanocobinamide at concentrations ranging from 100 nM to 100 µM. At the end of the incubation, the cells were washed rapidly four times with ice-cold phosphate-buffered saline (PBS), harvested with a rubber policeman, and collected by centrifugation for 15 sec at 10,000 g. The cell pellet was dissolved in 500 µl of 0.1 N NaOH, and radioactivity in sample aliquots was measured by liquid scintillation counting. Cobinamide uptake was linear between 2 and 15 min of incubation, and from $0.5-2 \times 10^6$ cells; counts obtained in zero time samples were <10% of those obtained in the 2 min samples.

Assessment of VASP Phosphorylation. Vasodilator-stimulated phosphoprotein (VASP) is expressed in a wide variety of cells (Reinhard et al., *Trends Biochem. Sci.* 26: 243-249, 2001); it is phosphorylated in response to NO and other vasodilators such as cGMP, with phosphorylation conveniently quantified by Western blotting since it retards the protein's gel mobility (Zhuang et al., *J. Biol. Chem.* 279: 10379-10407, 2004). Approximately $1 \times 10^6$ rat C6 glioma or CS-54 vascular smooth muscle cells in 12 well cluster dishes were transfected with 50 ng of an expression vector for VSV epitope-tagged VASP as previously described; C6 cells additionally received 25 ng cGMP-dependent protein kinase (G-kinase) I" expression vector (Zhuang et al., *J. Biol. Chem.* 279: 10379-10407, 2004; Gudi et al., *J. Biol. Chem.* 271: 4597-4600, 1996). The cells were cultured for 36 h in DME medium supplemented with 10% FBS, and were treated during the last 30 min with the indicated concentrations of the NO donor PAPA-NONOate (Cayman Chemical Co.) or the membrane-permeable cGMP analog 8-pCPT-cGMP (Biolog Inc.) in the case of C6 cells or the calcium ionophore A23187 (Calbiochem) in the case of CS-54 cells; some of the cultures received cobinamide or human hemoglobin (Danishpajooh et al., *J. Biol. Chem.* 276: 27296-27303, 2001)] simultaneous with the PAPA-NONOate. The cells were extracted in situ in a gel sample buffer containing 1% sodium dodecyl sulfate, and lysates were subjected to polyacrylamide gel electrophoresis and Western blotting. VASP was detected using a mouse anti-VSV monoclonal antibody (Sigma Chemical Co.) as previously described (Zhuang et al., *J. Biol. Chem.* 279: 10379-10407, 2004). The blots shown were reproduced at least three times.

Measurement of Nitrite and Nitrate. NO has a very short half-life, and is rapidly oxidized to nitrite and nitrate under physiological conditions. Hence, one of the most common methods for assessing NO production is to measure nitrite and nitrate concentrations, which is generally done using the Griess reagent (Danishpajooh et al., *J. Biol. Chem.* 276: 27296-27303, 2001; Idriss et al., *J. Biol. Chem.* 274: 9489-9493, 1999). Nitrite and nitrate concentrations were measured in both the *Drosophila Malpighian* tubule secretion system, and in the C6 and CS-54 cells. In the *Drosophila* system, 20 tubules were incubated in 100 µl of Schneider's medium, and the tubules were stimulated for 60 min with either 10 µM Deta-NONOate or 10 µM LPS, in the absence or presence of 10 µM cobinamide. The C6 and CS-54 cells were incubated for 30 min with 15 µM PAPA-NONOate and 300 nM A23187, respectively, in the absence or presence of 15 µM cobinamide. In all cases, the medium was collected at the end of the incubation period, and nitrite and nitrate in the medium were measured using the Nitric Oxide Quantitation Kit from Active Motif, which is an enhanced Griess reagent-based method. Because Deta-NONOate and PAPA-NONOate will continue to release NO even after the end of the incubation with the tubules and cells, all subsequent steps were performed at room temperature immediately after harvesting the medium.

Assessment of Cobinamide Cytotoxicity. The effect of varying concentrations of cobinamide on the growth of BHK, CS-54, and C6 cells, and human foreskin fibroblasts and human umbilical venous endothelial cells (HUVECs) was assessed by counting the number of cells daily for three days using a Model ZM Coulter Counter (Coulter Electronics). All of the cells were grown in DME containing 10% FBS, except the HUVECs, which were grown in M199 medium containing endothelial cell growth supplement and 20% FBS (Kim et al., *J. Biol. Chem.* 275: 33920-33928, 2000). Cells were plated in six well culture dishes at initial densities of $1.5-3 \times 10^5$ cells per well.

Measurement of the Activity of Methionine Synthase and Methylmalonyl-CoA Mutase in vitro. BHK cells were extracted as described previously at a density of approximately $50 \times 10^6$/ml in a buffer containing 100 mM Tris HCl, pH 7.4, 5 mM dithiothreitol, 1 mM EDTA, and a protease inhibitor cocktail (Idriss et al., *J. Biol. Chem.* 274: 9489-9493, 1999). Methionine synthase and methylmalonyl-CoA mutase activities were measured in the extracts in the absence and presence of 1-200 µM cobinamide. Methionine synthase activity was measured at 37° C. according to the method of Weissbach (Weissbach et al., *J. Biol. Chem.* 238: 3318-3324, 1963), except the [$^{14}$C]-methyl-tetrahydrofolate substrate was separated from the [$^{14}$C]-methionine product by thin layer chromatography on cellulose acetate plates developed in butanol:acetic acid:water (4:1:5); the Rf values for substrate and product were 0.26 and 0.44, respectively. For methylmalonyl-CoA mutase, the extracts were pre-incubated for 10 min at 37° C. with 5 µM deoxyadenosyl-cobalamin to convert apoenzyme to holoenzyme, followed by a 10-fold dilution in extract buffer. Enzyme activity was measured at 30° C. according to the method of Kikuchi (Kikuchi et al., *Clin. Chim. Acta* 184: 307-313, 1989), with the methylmalonyl-CoA substrate separated from the succinyl-CoA product by HPLC on a C18 reverse phase column eluted in 100 mM sodium phosphate, pH 4.0 containing 15% methanol; amounts of substrate and product were determined by comparison to known standards. Both assays were linear with time from 5-15 min, and with protein concentration from 0.1-0.5 mg/ml.

Assessment of the Activity of Methionine Synthase and Methylmalonyl-CoA Mutase In vivo. The activities of methionine synthase and methylmalonyl-CoA mutase were assessed in intact BHK cells by following incorporation of [$^{14}$C]-formate into purine nucleotides and [$^{14}$C]-propionic acid into protein, respectively; both of these assays have been used previously as surrogate measurements of the enzymes' in vivo activities (Danishpajooh et al., *J. Biol. Chem.* 276: 27296-27303, 2001; Willard et al., *Hum. Genet.* 32: 277-283, 1976). Briefly, about 1×10$^6$ BHK cells were incubated in six well cluster dishes with 10 µCi [$^{14}$C]-formate for 90 min or 20 µCi [$^{14}$C]-propionic acid for 16 h; cobinamide, at concentrations of 1-200 µM, was added 6_h prior to the formate label (for a total incubation time of 8 h) and simultaneous with the propionate label. At the end of the incubation, the cells incubated with [$^{14}$C]-formate were extracted in 0.4 N perchloric acid, heated to 100° C. for 70 min to convert purine nucleotides to bases, and applied to Dowex 50 cation exchange columns to separate the purine bases from unincorporated [$^{14}$C]-formate (Boss and Erbe, *J. Biol. Chem.* 257: 4242-4247, 1982). The cells incubated with [$^{14}$C]-propionic acid were extracted in ice-cold 10% trichloroacetic acid, heated to 80° C. for 30 min to solubilize precipitated nucleic acids, and after re-cooling to 4° C., precipitated protein was collected on glass microfiber filters (Boss and Erbe, *J. Biol. Chem.* 257: 4242-4247, 1982). Both assays were linear with time and cell number from 0.5–2×10$^6$ cells/ml.

2. Results

Figure 2:
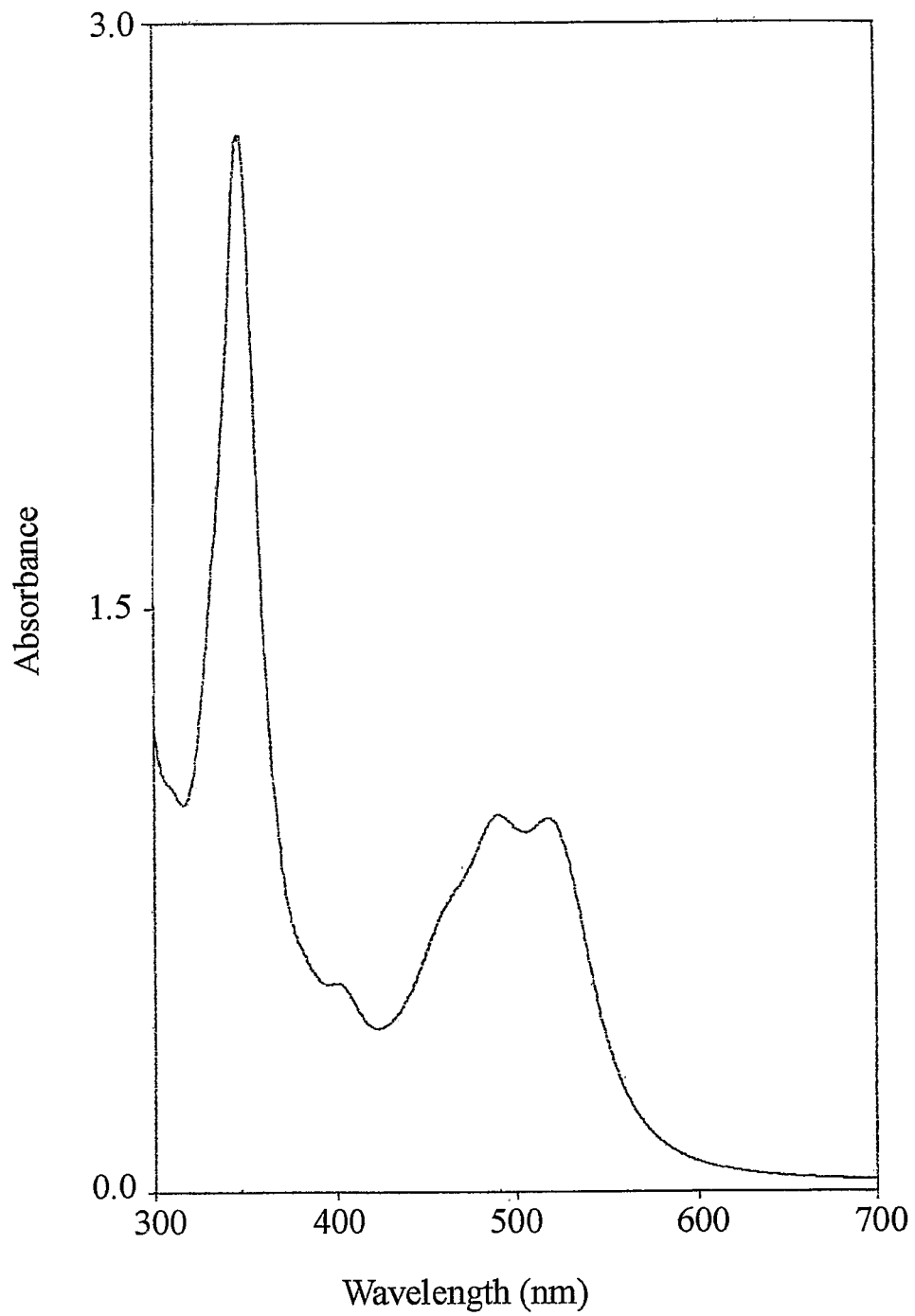
FIG. 2. Spectral Analysis of Cobinamide. Cobinamide was produced from hydroxocobalamin as described in Exemplary Embodiments, and was purified on a C18 solid phase extraction column. After concentration, the sample was brought to pH 3.0, and the spectrum of the diaquocobinamide product was recorded between 300 and 700 nm.

Production and Analysis of Cobinamide. The standard method for producing diaquocobinamide starts with dicyanocobinamide, removing the cyanide by acid treatment and exposure to strong light (Hayward et al., *J. Chem. Soc.* 6485-6493, 1965). As mentioned earlier, cobinamide has a very high binding affinity for cyanide, and hence it is difficult to completely remove cyanide from the cobinamide preparations. Moreover, exposure to light over a prolonged period can potentially alter the corrin ring. Hydroxocobalamin (OH-Cbl) was used as the initial substrate since the goal was to produce cyanide-free cobinamide for use in biological systems. The dimethylbenz-imidazole ribonucleotide tail was removed by brief acid treatment, and the diaquocobinamide was purified by batch elution over a small sample preparation column as described in Exemplary Embodiments. Beginning with about 200 mg of OH-Cbl, approximately 150-170 mg of high purity cobinamide was obtained. FIG. 2 shows the absorbance spectrum of a typical cobinamide preparation at pH 3 having a major peak of 348 nm, and smaller relatively equal peaks at 494 and 520 nm (Hayward et al., *J. Chem. Soc.* 6485-6493, 1965; Baldwin et al., *J. Chem. Soc. Dalton Trans.* 217-223, 1983); in preparations containing contaminants, the 494 and 520 nm peaks tend to either merge together into one broad peak or the 520 peak becomes predominant, and a broad band at 455 nm becomes evident (Ford et al., *J. Inorg. Biochem.* 41: 235-244, 1991). Further evidence for high purity of the preparations was that at pH 12 the A344/A356 absorbance ratio was 1.06, well within the range of 1.05-1.11 previously reported for pure dihydroxocobinamide (Ford et al., *J. Inorg. Biochem.* 41: 235-244, 1991), and HPLC analyses of the cobinamide product yielded a single peak when monitored at multiple wavelengths between 300 and 600 nm (Ford et al., *J. Chromatogr.* 536: 185-191, 1991).

Efficacy of Cobinamide as an NO Scavenger in a *Drosophila* Fluid Secretion Model. It has become clear that *Drosophila* is an excellent model for human disease and drug discovery (Tickoo and Russell, *Curr. Opin. Pharmacol.* 2: 555-560, 2002; O'Kane, *Semin. Cell Dev. Biol.* 14: 3-10, 2003). The Malpighian tubules of *D. melanogaster* are the insect's fluid transporting and osmoregulatory organ, corresponding to vertebrate kidneys. Rates of tubular secretion can be measured in vitro after extracting tubules from flies; NO stimulates secretion via activation of soluble guanylate cyclase, thereby increasing the intracellular cGMP concentration and activating the cGMP/G-kinase transduction pathway (Broderick, *Am. J. Physiol.* 285: C1207-C1218, 2003; Dow and Davies, *Physiol. Rev.* 83: 687-729, 2003). The effect of cobinamide on tubular fluid secretion stimulated both by an NO donor, and by LPS, an inducer of the *Drosophila* NOS gene was studied. In addition, to simulate conditions in a whole animal, cobinamide was administered to the flies via their food, and then measured the effect of LPS on rates of tubular fluid secretion.

Figure 3:
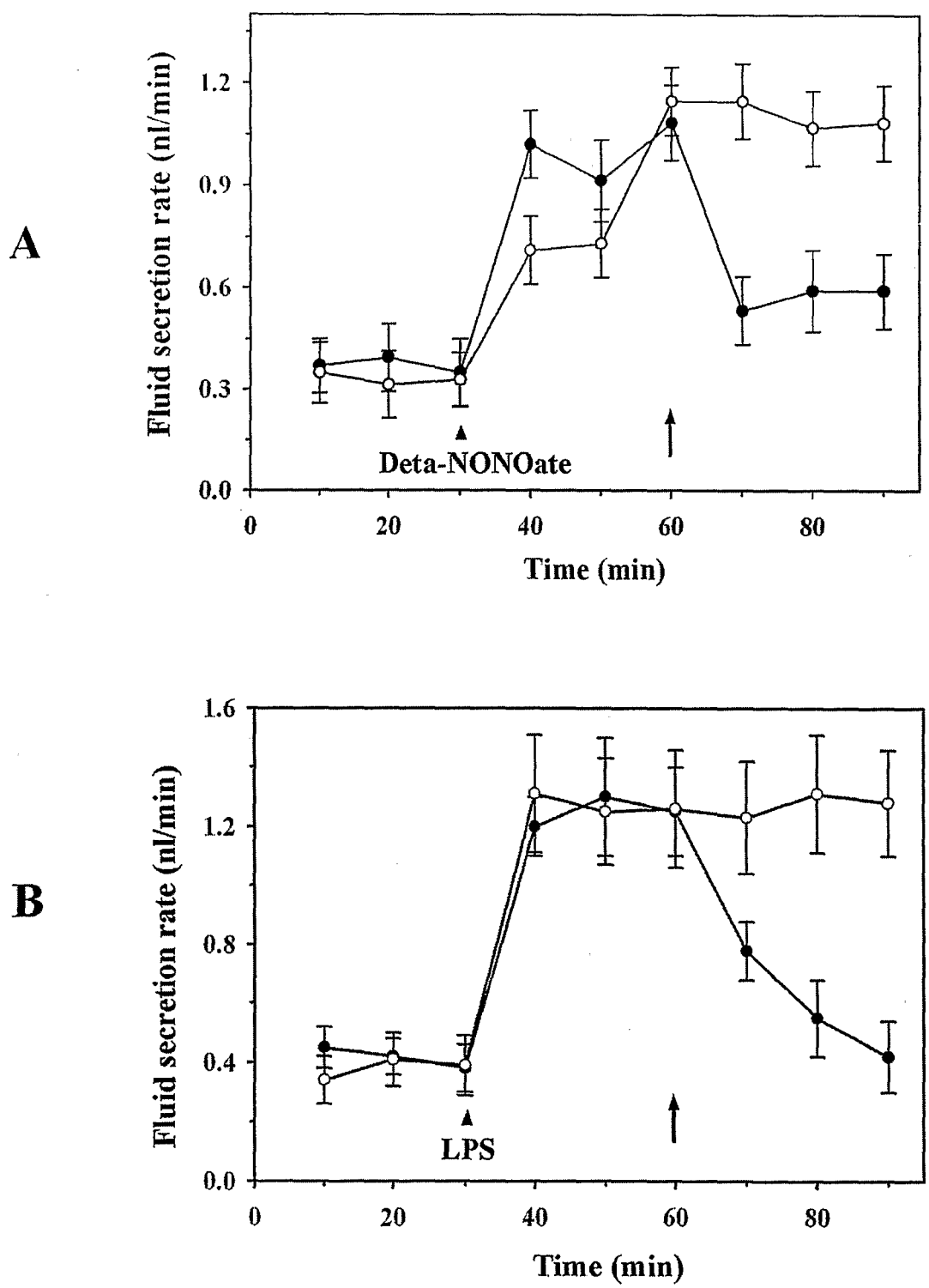
FIG. 3. Effect of Cobinamide on NO-stimulated Malpighian Tubule Secretion and Nitrite and Nitrate Concentrations. Panels A and B. Malpighian tubules were removed from wild type $D. melanogaster$ flies, and tubular secretion rates were determined by measuring droplet formation from the single ureter of a tubular pair over 10 min intervals. Basal tubular secretion rates were measured for 30 min, and then the tubules were treated with either 10 μM Deta-NONOate (Panel A) or 1 μM lipopolysaccharide (LPS, Panel B); in both panels, the time of drug addition is noted by an arrowhead. Cobinamide at a final concentration of 10 μM was added to some of the tubules at 60 min (drug addition noted by arrows in both panels A and B, and by the filled circles); some tubules received 10 μM cobinamide plus 10 μM cobalamin (filled triangles in both panels A and B). Each data point represents the mean ±standard deviation of at least three independent experiments performed on 20 pairs of Malpighian tubules. Panel C. Ten pairs of tubules were incubated in 200 μl of Schneider's medium for 60 min with either 10 μM Deta-NONOate or 10 μM LPS in the absence (open bars) or presence (filled bars) of 10 μM cobinamide (Cbi). Nitrite and nitrate in the medium were measured by a Griess reagent-based method, and were quantified by comparison to standards. The data are the mean ±standard deviation of at least two independent experiments performed in triplicate; the y axis on the left is for the Deta-NONOate data, and the y axis on the right is for the LPS data. No nitrite or nitrate could be detected in the medium from untreated tubules.
Figure 3:
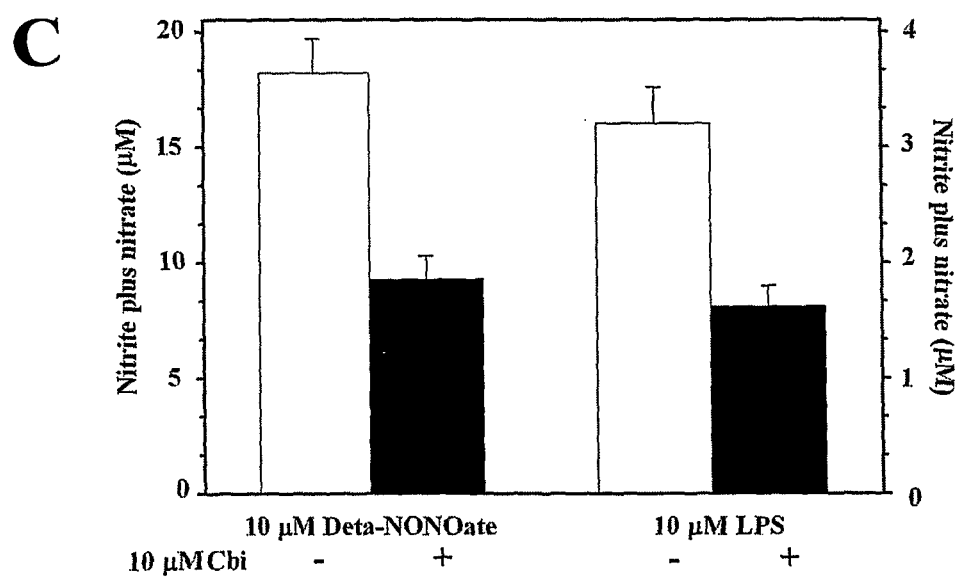

In the experiments with an NO donor, tubules were treated with 10 µM Deta-NONOate, which caused a rapid and sustained increase in the rate of fluid secretion (FIG. 3, panel A; Deta-NONOate was added to all tubules after a 30 min basal period, as indicated by the arrowhead). Adding 10 µM cobinamide to Deta-NONOate-treated tubules reduced the rate of fluid secretion significantly, almost returning to the basal unstimulated level (FIG. 3, panel A; cobinamide was added at 60 min to some of the tubules as indicated by the arrow, and the filled circles). Adding cobinamide alone to the tubules was without effect. To increase endogenous NO production by the tubules, LPS was used and a marked stimulation of tubular secretion was observed (FIG. 3, panel B; LPS was added at 30 min as indicated by the arrowhead). As in the experiments with Deta-NONOate, cobinamide rapidly reduced tubular secretion, returning rates near to the basal state (FIG. 3, panel B; cobinamide was added at 60 min to some of the tubules as indicated by the arrow, and the filled circles). Thus, cobinamide scavenges both extracellularly-administered and intracellularly-produced NO in a *Drosophila* whole organ system.

As part of these studies, the amount of NO released by Deta-NONOate or produced by LPS-treated tubules by incubating tubules for 60 min in Schneider's medium was measured, and measuring the sum of nitrite and nitrate in the medium. In the absence of the two drugs, no nitrite or nitrate could be detected in the medium, implying that the basal level of NO production by the tubules was very low. Treating the tubules with 1, 10, or 100 µM Deta-NONOate increased the nitrite and nitrate concentrations in the medium to levels above the starting concentrations of the drug, which was likely due to the fact that Deta-NONOate releases two moles of NO per mole of parent compound (FIG. 3C shows data for 10 µM Deta-NONOate). The tubules were probably exposed to somewhat lower NO concentrations, because as mentioned previously, Deta-NONOate will continue to release NO during the measurement of nitrite and nitrate. Treating the tubules with 10 µM LPS to induce NOS levels also increased medium nitrite and nitrate concentrations, but the levels were less than in the tubules treated with 10 µM Deta-NONOate (FIG. 3C). In both the Deta-NONOate- and LPS-treated tubules, cobinamide reduced the amount of combined nitrite and nitrate by about 50% (FIG. 3C), which is consistent with our previous work showing that each cobinamide molecule can neutralize two NO molecules, converting one to nitrite and binding the second one (Sharma et al., *Biochemistry* 42: 8900-8908, 2003); thus, a maximal 50% reduction in nitrite and nitrate could be expected.

Figure 4:
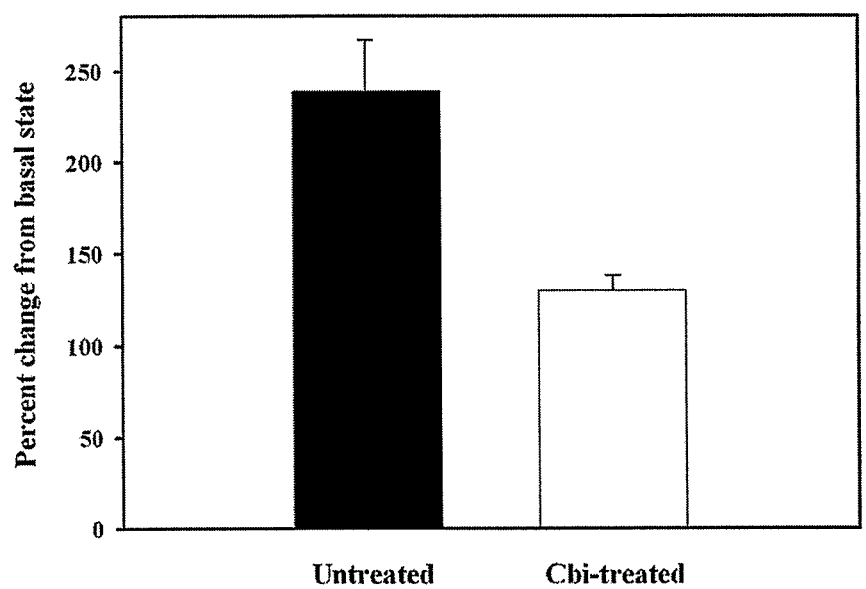
FIG. 4. Cobinamide-fed Flies Have an Attenuated Fluid Secretion Response to LPS. Wild type flies were grown for 48 h on either standard fly food or fly food containing 250 μM cobinamide (Cbi). Malpighian tubules from both control and cobinamide-fed flies were removed and used in a fluid secretion assay as described in FIG. 3. Basal secretion rates were measured for 30 min; the tubules were then stimulated with 1 μM lipopolysaccharide (LPS), and fluid secretion was measured for an additional 30 min. Results are expressed as the percent increase of the LPS-stimulated readings over basal readings, and are the mean ±standard deviation of three independent experiments.

To determine if systemically administered cobinamide would affect rates of tubular fluid secretion, the flies were fed food containing 250 µM cobinamide for two days; at this concentration, cobinamide had no apparent detrimental effect on the flies. LPS-stimulated secretion rates of Malpighian tubules were compared between cobinamide-fed flies and flies fed normal control food. Tubular secretion rates were reduced by about 50% in the cobinamide-fed flies compared to control flies (FIG. 4). In addition to providing further evidence for cobinamide's effectiveness as an NO scavenger, these data indicate that cobinamide was absorbed through the gut of the flies and was transported to the Malpighian tubules.

Cobinamide Uptake by Mammalian Cells. Some NO scavengers, such as hemoglobin, are solely extracellular and neutralize only that NO which diffuses out of cells. The studies in Drosophila indicated that cobinamide was likely taken up by the cells, but insect and mammalian transport systems can differ. To determine whether cobinamide has access to intracellular NO in mammalian cells, [$^{14}$C]-dicyanocobinamide was produced, and its uptake in BHK cells was studied. A progressive curve-linear increase in radioactivity in BHK cells over a 1000-fold concentration range of dicyanocobinamide from 100 nM to 100 µM suggesting that both passive diffusion and active transport of the dicyanocobinamide was occurring. Because of the progressive increase in cellular radioactivity, a $K_M$ could not be calculated. Although it is possible that the cobinamide was not actually taken up by the cells, but rather just bound to a surface receptor, this seems unlikely because of the continued increased in radioactivity over a three log scale of dicyanocobinamide concentrations. Thus, these data suggest that cobinamide has the potential to serve as both an intra- and extra-cellular NO scavenger in mammalian systems.

Efficacy of Cobinamide as an NO Scavenger in Mammalian Cells. To determine whether cobinamide can serve as an NO scavenger in mammalian cells, NO stimulation of VASP phosphorylation was studied in two different types of cultured cells. VASP is an important regulator of actin dynamics, and thus of cellular processes such as cell adhesion and motility (Zhuang et al., J. Biol. Chem. 279: 10379-10407, 2004). Its function is regulated by phosphorylation, and NO, via activation of the cGMP/G-kinase transduction pathway, is a major inducer of VASP phosphorylation. To study the effect of cobinamide on NO-induced phosphorylation of VASP, rat C6 glioma cells and CS-54 vascular smooth muscle cells were chosed, both of which have an active NO/cGMP transduction pathway (Idriss et al., J. Biol. Chem. 274: 9489-9493, 1999; Chen et al., Mol. Cell. Biol. 23: 4066-4082, 2003). The effect of cobinamide on exogenously-generated NO was studied in C6 cells, and the effect of cobinamide on endogenously-produced NO was studied in CS-54 cells.

Figure 5:
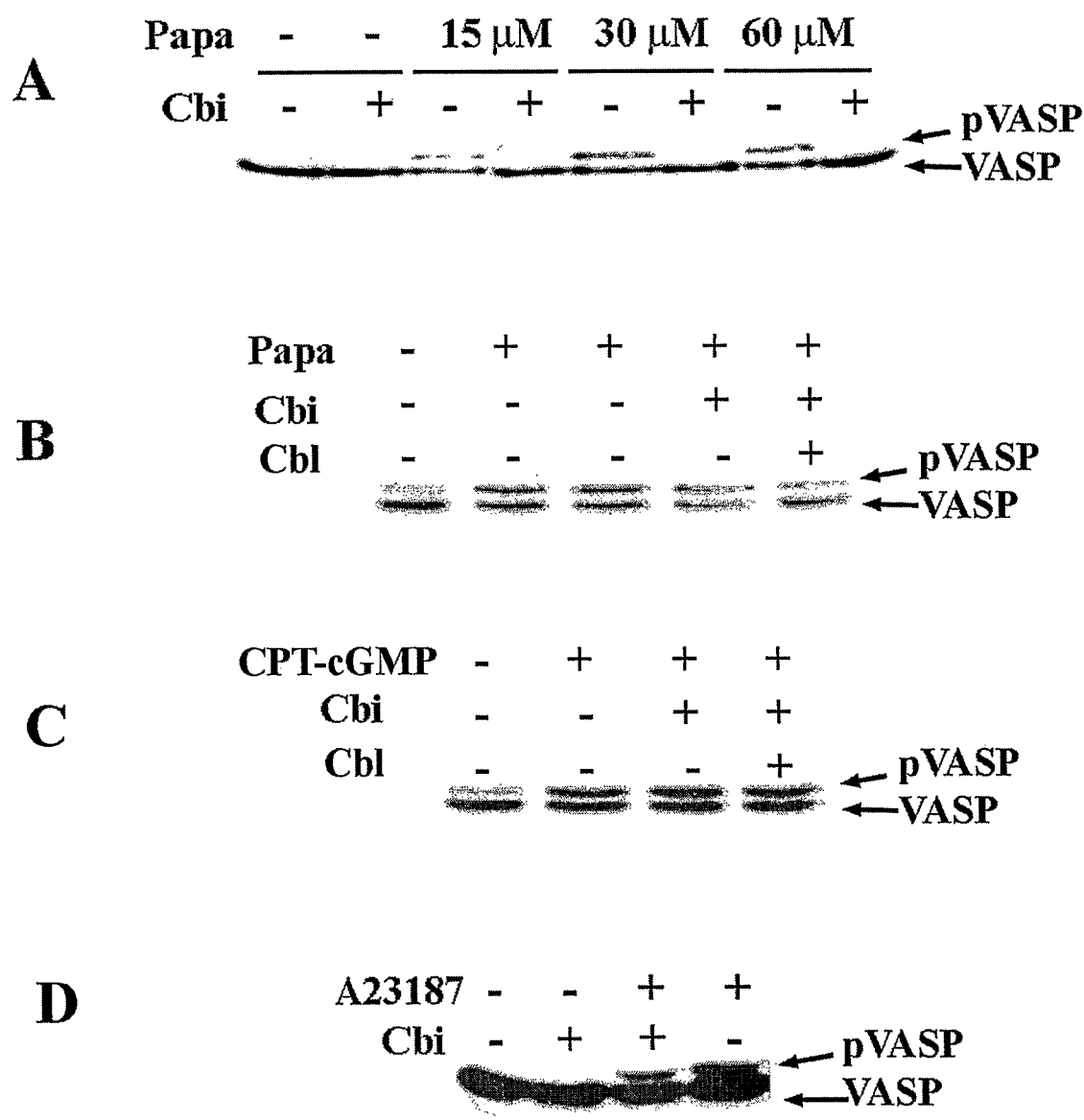
FIG. 5. Effect of Cobinamide on VASP Phosphorylation and Nitrite and Nitrate Concentrations. Rat C6 glioma cells (panels A-C) and CS-54 vascular smooth muscle cells (panel D) were transfected with an expression vector encoding VSV epitope-tagged VASP; C6 cells were co-transfected with G-kinase I. The cells were extracted 16 h later, and the extracts were subjected to Western blotting using a monoclonal anti-VSV antibody. Panel A. Cells were left untreated (lane 1) or were treated for 30 min prior to extraction with 100 µM cobinamide (Cbi, lanes 2, 4, 6, and 8), and/or the NO donor PAPA-NONOate (Papa) at 15 (lanes 3 and 4), 30 (lanes 5 and 6), or 60 µM (lanes 7 and 8). Phosphorylated VASP (pVASP) migrates more slowly than non-phosphorylated VASP. Panel B. Cells were left untreated (lane 1) or were treated for 30 min prior to extraction with 30 µM PAPA-NONOate (Papa) (lanes 2-5); some cells additionally received 30 µM cobinamide (lane 4) or 30 µM cobinamide plus 30 µM cobalamin (lane 5). Panel C. Cells were left untreated (lane 1) or were treated for 30 min prior to extraction with 30 µM 8-pCPT-cGMP (lanes 2-4) with 30 µM cobinamide (lane 3) or the combination of 30 µM cobinamide and 30 µM cobalamin (lane 4). Panel D. CS-54 cells were left untreated (lane 1) or were treated for 60 min prior to extraction with 100 µM cobinamide (lanes 2 and 3), and/or 100 nM of the calcium ionophore A23187 (lanes 3 and 4). Panel E. C6 cells (left-half of graph) and CS-54 cells (right-half of graph) were treated for 30 min with 15 µM PAPA-NONOate and 300 nM A23187, respectively. Half of the cultures additionally received 15 µM cobinamide (filled bars). The medium was harvested, and the sum of nitrite plus nitrate was measured as described in the legend to FIG. 3. The data are the mean ±standard deviation of at least two independent experiments performed in triplicate; the y axis on the left is for the PAPA-NONOate-treated C6 cells, and the y axis on the right is for the A23187-treated CS-54 cells. Low nitrite and/or nitrate concentrations in the medium of untreated cells were subtracted from that of the treated cells.
Figure 5:
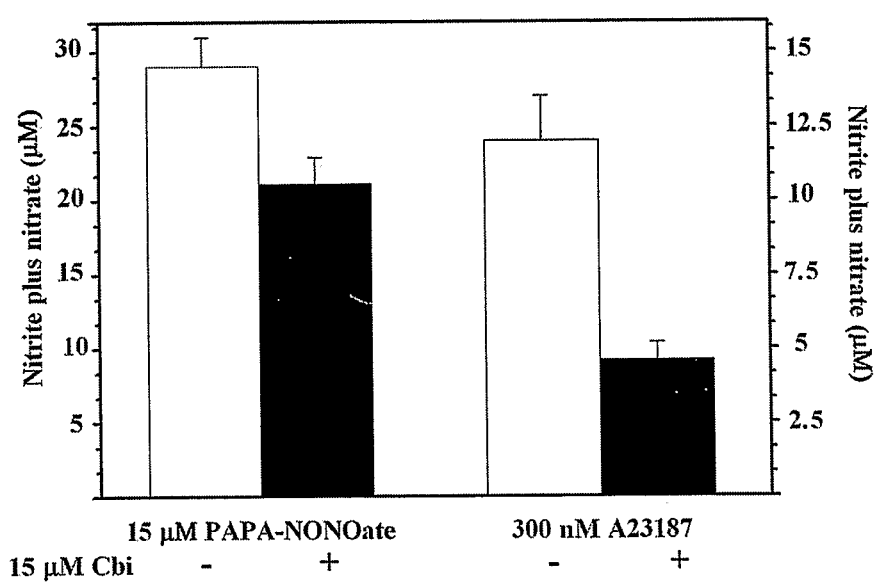

When C6 cells were treated for 30 min with 15 to 60 µM of the NO-releasing compound PAPA-NONOate, VASP phosphorylation was induced, as evidenced by generation of a VASP form with reduced electrophoretic mobility (FIG. 5A, compare lane 1, no PAPA-NONOate, to lanes 3, 5, and 7 showing 15, 30, and 60 µM PAPA-NONOate, respectively). At all PAPA-NONOate concentrations, adding 100 µM cobinamide to the culture medium prevented the increase in VASP phosphorylation (FIG. 5A, compare lanes 3, 5, and 7 to lanes 4, 6, and 8 showing cells treated with cobinamide and PAPA-NONOate). Human hemo-globin (100 µM) yielded similar results as cobinamide, indicating that under the experimental conditions, cobinamide and hemoglobin were equally effective NO scavengers. Cobinamide also prevented increases in VASP phosphorylation when used at an equimolar concentration as PAPA-NONOate (FIG. 5, panel B shows 30 µM each of PAPA-NONOate and cobinamide, but similar results were also found at 15 and 60 µM of each agent). As discussed further below, PAPA-NONOate releases two moles of NO, and thus as in the Drosophila Malpighian tubules, each cobinamide molecule appeared to neutralize two NO molecules.

Because it was possible that cobinamide could be inhibiting the NO stimulation of VASP phosphorylation through some mechanism other than NO scavenging, the effects of cobinamide on cGMP stimulation of VASP phosphorylation was studied. The membrane-permeable cGMP analog 8-pCPT-cGMP at a concentration of 30 µM to induce VASP phosphorylation was measured, and found no effect of cobinamide at concentrations from 30 to 100 µM (FIG. 5, panel C, compare lane 2, CPT-cGMP alone, to lane 3, CPT-cGMP plus cobinamide). Thus, cobinamide did not interfere with the activation of G-kinase or the phosphorylation of VASP, and thus, it appeared to be acting via NO scavenging.

Since calcium activates Types I and III NOS, CS-54 cells were treated with the calcium ionophore A23187 to increase endogenous NO production. A23187 was found to increase VASP phosphorylation (FIG. 5D, compare lane 4 to lane 1), and that cobinamide significantly attenuated this effect (FIG. 5D, compare lane 3 to lane 4). Thus, cobinamide is an effective intra- and extra-cellular NO scavenger in mammalian cells.

As in the studies of the Malpighian tubules, nitrite and nitrate concentrations in the culture medium of the C6 and CS-54 cells were measured. As mentioned above, PAPA-NONOate, like Deta-NONOate, releases two NO molecules per mole of parent compound, and treating C6 cells for 30 min with 15 µM PAPA-NONOate was found to increase the concentration of nitrite and nitrate in the medium to almost 30 µM (when compared to untreated cells, FIG. 5E). Because of the short half-life of PAPA-NONOate—15 min at 37° C.—the vast majority of the NO was released during the incubation period, and not during the subsequent measurement of nitrite and nitrate. Treating CS-54 cells with 300 nM A23187 increased nitrite and nitrate concentrations in the medium to about 12 µM (FIG. 5E). When 15 µM cobinamide was added to the PAPA-NONOate-treated C6 cells or the A23187-treated CS-54 cells, there was a significant decrease in the nitrite plus nitrate concentrations, with a larger effect in the CS-54 cells than in the C6 cells (FIG. 5E). Thus, the cobinamide-induced decrease in VASP phosphorylation in the two cell types was reflected by a reduction in nitrite and nitrate, providing further evidence that cobinamide was functioning as an NO scavenger in reducing VASP phosphorylation.

Figure 6:
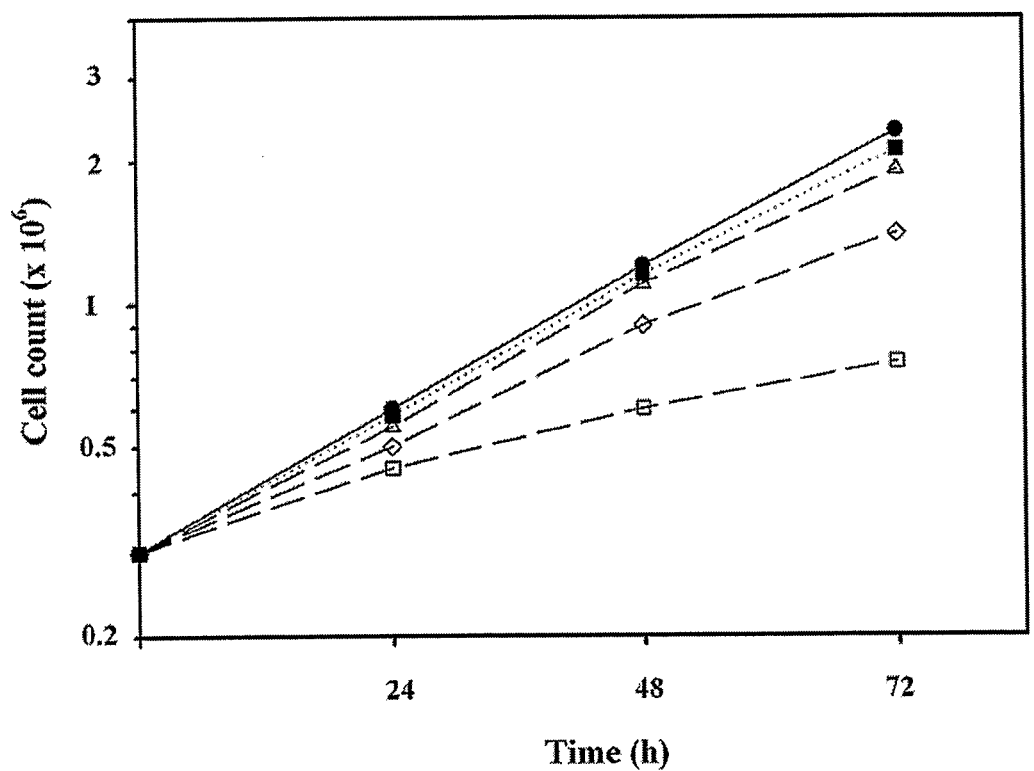
FIG. 6. Effect of Cobinamide on Growth of BHK, C6, and CS-54 Cells. BHK, C6, and CS-54 cells were plated at densities of $1.5-3\times10^5$ cells per well of six well culture dishes in DME medium supplemented with 10% FBS, and were counted daily for three days. Cells were cultured in the absence of cobinamide (uninterrupted line, filled circles) or in the presence of 50 µM, 100 µM, or 200 µM cobinamide (dashed lines with open triangles, diamonds, and squares, respectively). The main figure shows the data for BHK cells, and the inset shows the data for C6 and CS-54 cells. Some of the BHK cells with 200 µM cobinamide also received 200 µM cobalamin (dotted line, filled squares). The data are the means of duplicate cultures from a representative experiment.

Studies of Cobinamide Cytotoxicity. As a cobalamin analog, cobinamide could be cytotoxic by interfering with cobalamin metabolism or function. Moreover, as an NO scavenger, cobinamide could interfere with the pro-proliferative and anti-apoptotic actions of NO in some cell types (Morbidelli et al., Am. J. Physiol. 270: H411-415, 1996; Ha et al., FASEB J. 17: 1036-1047, 2003). To study the potential toxicity of cobinamide in mammalian cells, several sets of experiments were performed. Ccobinamide's effect on the growth of BHK, C6, and CS-54 cells, as well as two primary human cell lines, i.e., foreskin fibroblasts and HUVECs; the latter cells were included to determine if there was differential toxicity of cobinamide to primary cells than to established cell lines were assessed. At concentrations between 1 and 50 µM, cobinamide had no effect on cell growth, but at concentrations 50 µM, cobinamide inhibited the growth of all five cell types, albeit by a minimal amount at 50 µM (FIG. 6, data shown at cobinamide concentrations of 50, 100, and 200 µM in BHK cells, and C6 and CS-54 cells (inset); similar results were found in the two primary cell lines). Growth inhibition was reversed completely by an equimolar concentration of cobalamin at all three cobinamide concentrations in all five cell types (FIG. 6; data shown for 200 µM cobinamide/cobalamin in BHK cells (main figure). These latter data suggest that the mechanism of toxicity was through competitive interference of cobalamin metabolism or function, rather than through NO scavenging. Thus, cobinamide was toxic to cells at only relatively high concentrations, and its toxicity could be reversed fully by cobalamin.

The next set of experiments was directed at determining whether cobinamide inhibited the activities of either methionine synthase or methylmalonyl-CoA mutase, the two vitamin $B_{12}$-dependent enzymes in mammalian cells. At concentrations as high as 200 µM, no effect of cobinamide on the activities of either enzyme as measured in BHK cell extracts was found. Methionine synthase was assumed to be in the holoenzyme form (Oltean and Banerjee, J. Biol. Chem. 278: 20778-20784, 2003), and methylmalonyl-CoA mutase apoenzyme was converted to holoenzyme by incubation with 5 µM deoxyadenosyl-cobalamin followed by a 10-fold dilution of the extract as described in Exemplary Embodiments. Thus, at the highest concentration of cobinamide tested, the cobinamide concentration was 400 times that of the deoxyadenosyl-cobalamin concentration. The lack of inhibition of either enzyme by cobinamide is consistent with studies reported by others on various cobalamin analogs including cobinamide (Kolhouse et al., J. Biol. Chem. 266: 23010-23015, 1991; Stabler et al., J. Clin. Invest. 87: 1422-1430, 1991).

Figure 7:
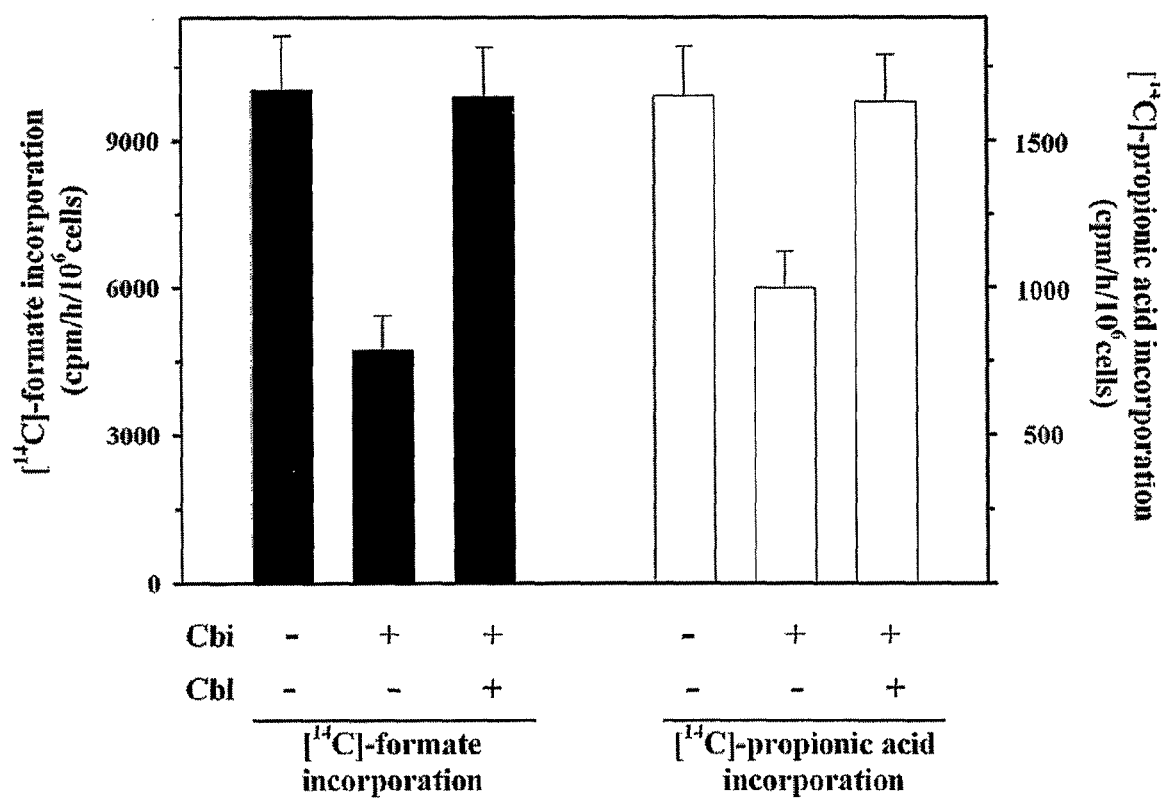
FIG. 7. Effect of Cobinamide on In vivo Activities of Methionine Synthase and Methylmalonyl-CoA Mutase. BHK cells were cultured in DME medium containing 10% FBS in six well culture dishes. The cells were cultured with either 10 µCi of [$^{14}$C]-formate (filled bars) or [$^{14}$C]-propionic acid (open bars) for 90 min or 16 h, respectively. Cobinamide (Cbi) at a concentration of 100 µM was added 6½ h prior to the formate label and simultaneously with the propionic acid label as indicated. Some cultures additionally received 100 µM cobalamin (Cbl) at the time of cobinamide addition. At the end of the incubation period, the cells were extracted in either 0.4 N perchloric acid (formate label) or 10% trichloroacetic acid (propionic acid label) and processed as described in Exemplary Embodiments. The data are the mean ±standard deviation of at least three independent experiments performed in duplicate. Formate incorporation assesses in vivo methionine synthase activity, and propionic acid incorporation assesses in vivo methylmalonyl-CoA mutase activity.

In the final set of experiments, the effect of cobinamide on the in vivo activities of methionine synthase and methylmalonyl-CoA mutase following the incorporation of [$^{14}$C]-formate into purine nucleotides and [$^{14}$C]-propionic acid into protein was assessed; the former assay is a measure of carbon flux through the folate pathway and is dependent on methionine synthase activity, while the later assay is dependent on methylmalonyl-CoA mutase activity. In both assays, 100 µM cobinamide decreased incorporation of the radioactive label by about 50% (FIG. 7; filled bars are data for [$^{14}$C]-formate incorporation, and open bars are data for [$^{14}$C]-propionic acid incorporation). The inhibition of enzyme activities was time-dependent, and in the case of methionine synthase, minimal inhibition was observed after 90 min of cobinamide exposure, the shortest time point that could be measured; inhibition increased progressively with time, and the data in FIG. 7 are for a total of 8 h of cobinamide exposure. Similar time dependence of enzyme inhibition was observed for methylmalonyl-CoA mutase, but over a longer time scale. As in the growth studies, the toxic effect of cobinamide was completely prevented by an equimolar concentration of cobalamin (FIG. 7). These latter data indicate that the mechanism of cobinamide toxicity is likely through interference with some aspect of cobalamin metabolism (as considered further in the Discussion). Moreover, since methionine synthase and methylmalonyl-CoA mutase are the only two mammalian cobalamin-dependent enzymes, the cobalamin-reversal data suggest that the [$^{14}$C]-formate and [$^{14}$C]-propionic acid incorporation assays accurately reflect the in vivo activity of these two enzymes.

Efficacy of Cobinamide as an NO Scavenger in the Presence of Cobalamin. Although cobinamide is likely to be used at concentrations where it is not toxic, it would be useful to know whether cobinamide and cobalamin can be used together when scavenging NO. Cobalamin itself is a weak NO scavenger (Greenberg et al., J. Pharmacol. Exp. Ther. 273: 257-265, 1995), and would not be expected to interfere with cobinamide's scavenging of NO. OH-Cbl had no effect on NO scavenging by cobinamide, either on tubular fluid secretion in Drosophila Malpighian tubules (FIG. 3, panels A and B, compare filled circles, cobinamide alone, to filled triangles, cobinamide plus cobalamin) or on VASP phosphorylation in mammalian cells (FIG. 5, panel B, compare lane 4, cobinamide alone, to lane 5, cobinamide plus cobalamin). The combination of cobinamide plus cobalamin, like cobinamide alone, had no effect on VASP phosphorylation induced by 8-pCPT-cGMP (FIG. 5, panel C, compare lanes three and four).

3. Discussion

Since NO's original description as endothelium-derived relaxation factor in 1978, it has become clear that NO has many physiological roles (Lloyd-Jones and Bloch, Annu. Rev. Med. 47: 365-375, 1996; Ignarro and Murad, (1995) Nitric oxide. Biochemistry, molecular biology and therapeutic implications, Academic Press, San Diego; Hölsher, Trends Neurosci. 20: 298-303, 1997). It also has become clear that NO contributes to the pathophysiology of several disease states including septic and hemorrhagic shock, hepatic encephalopathy, hepatorenal syndrome, hemodialysis-related hypotension, and ischemia-reperfusion injury (Shah et al., Gastroenterology 126: 903-913, 2004; Komeno et al., J. Vet. Med. Sci. 66: 53-57, 2004; Pfeilschifter et al., Pflugers Arch. 442: 479-486, 2001). In most of these diseases, abnormally high NO production induces profound vasodilation and vasopressor-refractory hypotension. A marked increase in iNOS underlies the elevated NO production in sepsis (Moncada and Higgs, New Eng. J. Med. 329: 2002-2012, 1993), and non-selective NOS inhibitors increase blood pressure in animal models of sepsis, but have had a mixed effect on sepsis-associated mortality in animals and humans (Kim and Greenburg, Shock 17: 423-426, 2002; Vincent et al., Am. J. Respir. Crit. Care Med. 161: 1781-1785, 2000); this can relate, in part, to inhibition of eNOS leading to microvascular vasoconstriction and decreased tissue and organ perfusion (Spain et al., J. Trauma 36: 720-725, 1994; Wright et al., Cardiovasc. Res. 26: 48-57, 1992; Shultz and Raij, J. Clin. Invest 90: 1718-1725, 1992; Harbrecht et al., J. Leukoc. Biol. 52: 390-394, 1992; Tribl et al., Am. J. Physiol 286: H340-H345, 2004). Selective iNOS inhibitors should avoid some of the problems encountered with non-specific inhibitors, but iNOS expression in some tissues can be functionally important as has been found for myocyte iNOS (Poon et al., Circulation 108: 1107-1112, 2003; Ichinose et al., Am. J. Physiol. 285: H2524-H2530, 2003; Szabo et al., Proc. Natl. Acad. Sci. U.S.A 91: 12472-12476, 1994; Liaudet et al., J. Infect. Dis. 177: 127-132, 1998; Price et al., Eur. J. Pharmacol. 472: 111-118, 2003). Thus, even selective iNOS inhibition can lead to dysfunctional changes in cells and organs, and several groups of workers have urged caution in using any type of NOS inhibitor in sepsis (Vincent et al., Am. J. Respir. Crit. Care Med. 161: 1781-1785, 2000, Hotchkiss et al., Lancet 339: 434-435, 1992; Cobb, Crit. Care Med. 27: 855-856, 1999).

There is a clear need, therefore, for agents which can lower NO levels without the attendant toxicity of NOS inhibitors. NO scavengers have the theoretical advantage of neutralizing only the portion of pre-synthesized NO to which the agent is exposed, without directly interfering with NOS function (Kim and Greenburg, Shock 17: 423-426, 2002; Heneka et al., J. Clin. Invest 99: 47-54). Several NO scavengers have been identified, but not all are taken up by cells, and some, particularly free hemoglobin, exhibit unacceptable toxicity (Braun et al., J. Exp. Med. 131: 443-460, 1970). Thus, there would appear to be the need for a non-toxic NO scavenger that could be used both clinically and in the laboratory.

Cobinamide was found to be an effective NO scavenger, both in a Drosophila tubular secretion model and in two types of cultured mammalian cells. In both systems, each cobinamide molecule appeared to neutralize more than one NO molecule, which is in agreement with our previous in vitro work (Sharma et al., *Biochemistry* 42: 8900-8908, 2003). While the previous work was performed in aqueous buffers, the current work was performed in serum-containing medium, and found that cobinamide binds tightly to serum albumin, both bovine and human. Thus, cobinamide's binding to serum albumin does not appear to interfere with its ability to scavenge NO.

During bacterial biosynthesis of cobalamin, the dimethylbenzimidazole ribonucleotide tail is added last, and thus cobinamide is the penultimate precursor in cobalamin biosynthesis. Because of its place in cobalamin synthesis, cobinamide has been shown to contaminate bacterial vitamin $B_{12}$ preparations, and to be present in animal tissues and human serum (Kondo et al., *J. Clin. Invest* 70: 889-898, 1982; Kondo et al., *Proc. Natl. Acad. Sci. U.S.A* 77: 817-821, 1980; Kolhouse et al., *N. Engl. J. Med.* 299: 785-792, 1978). In a study of the enterohepatic circulation of corrinoids in humans, it was found that cobalamin analogues, which appeared to be mostly cobinamide, constituted 45% of total bile corrinoids (El Kholty et al., *Gastroenterology* 101: 1399-1408, 1991). A detailed study of the pharmacokinetics of cobinamide and cobalamin after parenteral administration to rabbits found that cobinamide was retained more by the liver than cobalamin, but that the urinary and fecal excretion of the two corrinoids was similar (Kolhouse and Allen, *J. Clin. Invest* 60: 1381-1392, 1977). Cobinamide binds poorly to transcobalamin II, the major cobalamin binding protein in blood, but it binds tightly to haptocorrin, another important cobalamin binding protein previously referred to as R binder (Fedosov et al., *Biochemistry* 34: 16082-16087, 1995; Kanazawa et al., *Proc. Soc. Exp. Biol. Med.* 183: 333-338, 1986; Fedosov et al., *J. Biol. Chem.* 277: 9989-9996, 2002). Thus, cobinamide's presence in serum and tissues, and its pharmacokinetic profile, are likely attributable to its high binding affinity for haptocorrin and possibly also albumin.

Previous studies have found little or no toxicity of cobinamide to mammalian cells, but these studies were done at low micromolar or sub-micromolar concentrations of the drug (Stabler et al., *J. Clin. Invest.* 87: 1422-1430, 1991; Kondo et al., *Int. J. Hematol.* 56: 167-177, 1992; Weinberg et al., *Biochem. Biophys. Res. Commun.* 246: 393-397, 1998). Similarly, no toxicity of cobinamide to mammalian cells at low micromolar concentrations was found, but began to observe toxicity at a concentration of about 50 µM. Since each cobinamide molecule can potentially neutralize two NO molecules (Sharma et al., *Biochemistry* 42: 8900-8908, 2003), cobinamide can be able to neutralize NO concentrations up to 100 µM before exhibiting significant toxicity. Other than during pharmacological administration of NO, it is unlikely that NO concentrations ever exceed 10 µM under physiological conditions (Pfeilschifter et al., *Pflugers Arch.* 442: 479-486, 2001; Clancy and Abramson, *Proc. Soc. Exp. Biol. Med.* 210: 93-101, 1995; Poon et al., *Circulation* 108: 1107-1112, 2003). Moreover, cobalamin was found to completely prevente cobinamide toxicity, and that cobalamin did not interfere with NO scavenging by cobinamide, either in the *Drosophila* Malpighian tubule secretion model or in mammalian cells; as mentioned previously, cobalamin itself is an NO scavenger (Greenberg et al., *J. Pharmacol. Exp. Ther.* 273: 257-265, 1995).

At the relatively high concentrations where cobinamide began to exhibit toxicity, it appeared to interfere with cobalamin metabolism or function. This conclusion is based on the findings that cobinamide had no effect on the in vitro activities of methionine synthase and methylmalonyl-CoA mutase, the two mammalian cobalamin-dependent enzymes, while it inhibited in vivo assays of the enzymes in a time-dependent and cobalamin-reversible fashion. In the in vitro assays, the enzymes were in the cobalamin-containing holoenzyme form, indicating that cobinamide cannot compete with the bound cofactor. Other workers have also found no inhibition in vitro of the holoenzyme form of methionine synthase by cobalamin analogs, and in fact, cobinamide can restore the methionine synthase apoenzyme to full activity, but whether this occurs in vivo is not known (Kolhouse et al., *J. Biol. Chem.* 266: 23010-23015, 1991). The effect of cobalamin analogs on methylmalonyl-CoA mutase activity has apparently not been studied, but 5'-deoxyadenosyl-cobinamide is inactive in restoring function to the apoenzyme of methylmalonyl-CoA mutase (Chowdhury and Banerjee, *Biochemistry* 38: 15287-15294, 1999). The time-dependent inhibition of enzyme activity in the in vivo assays occurred over hours suggesting that newly synthesized enzyme was inhibited; the half-life of methionine synthase is about 12 h and that of methylmalonyl-CoA mutase appears to be approximately 30 h (Oltean and Banerjee, *J. Biol. Chem.* 278: 20778-20784, 2003; Riedel et al., *Biochem. J.* 341: 133-138, 1999). Thus, cobinamide could interfere with incorporation of methylcobalamin or deoxyadenosyl-cobalamin into newly synthesized methionine synthase and methylmalonyl-CoA mutase, respectively, or perhaps more likely, with the cellular transport of hydroxocobalamin or its conversion to the two coenzyme forms. Similar conclusions about the mechanism of toxicity of cobalamin analogs were reached previously (Kolhouse et al., *J. Biol. Chem.* 266: 23010-23015, 1991). Whatever the precise mechanism(s) of cobinamide cytotoxicity is, it can be completely prevented by co-administration of cobalamin.

Because of its high binding affinity for cyanide, cobinamide can also be expected to be an excellent cyanide scavenger, and can be used in clinical states of cyanide toxicity, e.g., smoke inhalation and nitroprusside toxicity. Cobalamin, which has a binding affinity for cyanide several orders of magnitude less than that of cobinamide, has already been shown to be effective in cyanide toxicity and is used for this purpose in France (Forsyth, *J. Toxicol. Clin. Toxicol.* 31: 277-294, 1993; Hall and Rumack, *J. Emerg. Med.* 5: 115-121, 1987; Zerbe and Wagner, *Crit. Care Med.* 21: 465-467, 1993).

Cobinamide can be an effective NO scavenger in *Drosophila* Malpighian tubules and cultured mammalian cells, and is useful in animal studies. It can also be beneficial in clinical states of excess NO and in cyanide toxicity, and can be combined with cobalamin in various therapeutic regimens.

B. Cyanide Toxicity and Cobinamide

1. Materials and Methods

Production of Cobinamide. Cobinamide was produced by acid hydrolysis of cobalamin (Sigma) as described above (Broderick et al., *J. Biol. Chem.* 280: 8678-8685, 2005); throughout the exemplary embodiments and as disclosed herein, "cobinamide" and "cobalamin" refer to their hydroxo derivatives. The purity of cobinamide was assessed spectrophotometrically, and by elution as a single peak by high performance liquid chromatography on a reversed phase column with the eluent monitored by UV absorption at 348 nm (Broderick et al., *J. Biol. Chem.* 280: 8678-8685, 2005). Potassium cyanide (Fisher Scientific) was dissolved in 10 mM NaOH, and in the experiments shown in FIG. 9C, was diluted into 10 mM $Na_2CO_3$, pH 9.5 prior to use. Wild type Oregon R *Drosophila melanogaster* from Bloomington Stock Center were used at room temperature as described above (Broderick et al., *J. Biol. Chem.* 280: 8678-8685, 2005). Chinese hamster lung fibroblasts (Chinese hamster cells) obtained from the American Type Culture Collection (CCL 16) were grown at 37° C. as described previously (Yadava et al., *J. Biol. Chem.* 277: 21221-21230, 2002). Beveled 33 gauge needles and 2.5 µl syringes were from Hamilton Company.

Measurement of Respiratory Activity of Chinese Hamster Cells. Mitochondrial respiratory activity of Chinese hamster cells was assessed by measuring oxygen consumption as described previously (Yadava et al., *J. Biol. Chem.* 277: 21221-21230, 2002). Briefly, cells were harvested by trypsinization, resuspended in 20 mM Hepes, pH 7.1, 250 mM sucrose, 10 mM $MgCl_2$, and permeabilized with 100 mg/ml digitonin. An amount of permeabilized cells corresponding to ~0.5 mg of protein was transferred to a metabolic chamber maintained at 37° C.; the chamber was filled completely with the Hepes-sucrose-$MgCl_2$ buffer, and care was used to assure no air bubbles were present. Cellular oxygen consumption was measured polarographically with a Clark oxygen electrode under basal conditions, after stimulation by 5 mM sodium succinate and glycerol 3-phosphate, and after adding 250 µM KCN followed by an equimolar amount of cobinamide or cobalamin.

Measurement of Growth of Cyanide-Treated Chinese Hamster Cells. Cells were grown in glucose-free Dulbecco's modified Eagle's medium supplemented with 25 mM galactose and 10% fetal bovine serum as described previously (Soderberg et al., *Somat. Cell Genet.* 5: 225-240, 1979). After 24 h of equilibration in the medium, 100 µM KCN was added (referred to as zero time); KCN was additionally added at eight and 24 h, and cells were counted at 48 h using a Model ZM Coulter Counter. To some cultures 10 µM cobinamide and cobalamin were added at zero time.

Delivery of Cobinamide and Cobalamin to *D. melanogaster*. Ingestion of Cobinamide and Cobalamin. Flies were grown on food containing 100 µM cobinamide or 100 µM cobalamin as described previously (Broderick et al., *J. Biol. Chem.* 280: 8678-8685, 2005). Briefly, standard fly food paste was liquified by heating to 40° C., and after adding cobinamide or cobalamin to final concentrations of 100 µM, the food was cooled to room temperature. Flies were grown on the cobinamide- or cobalamin-supplemented medium from the first instar larval stage prior to use in experiments. No toxicity from either agent was observed, even when flies were grown for more than 10 generations on the supplemented food.

Injection of Cobinamide and Cobalamin. Flies anesthetized on ice were injected into the thorax with 1 µl of water, or 1 µl of 500 µM cobinamide or cobalamin dissolved in water using a 33 gauge needle attached to a 2.5 µl syringe. They were allowed to recover for 10 min, and then were exposed to HCN as described below. In some experiments, they were exposed to HCN first, and then were injected within one minute of HCN exposure.

Inhalation of Cobinamide and Cobalamin. The mouthpiece of a commercially available nebulizer (EasyMist, Prestige Medical) was attached to a 1×3 cm (w×l) chamber, constructed of plastic tubing; gauze with cotton wool at the proximal end of the chamber reduced the rate of air flow and minimized turbulence. Flies were transferred to the chamber, and after a 10 min equilibration period, the nebulizer containing 100 µM cobinamide or 100 µM cobalamin was started. After 2 min of nebulization, the flies were allowed to recover for 2 min, and then were transferred to a new vial.

Exposure of *Drosophila melanogaster* to HCN and KCN.

Exposure to HCN. Flies were transferred to a 10 ml plastic vial, and after a 10 min equilibration period, HCN was generated in the vial by spotting 1 ml of a 1 or 10 mM KCN solution on a 0.5×0.5 cm square of Whatman #1 filter paper, which was placed immediately in the vial. The vial was shaken gently for 20 sec to force the insects to fly and open their respiratory spiricles, and after a 1 min total HCN exposure, the paper square was removed. The HCN caused all flies, including those previously treated with cobinamide or cobalamin, to fall to the bottom of the vial unconscious. Flies were monitored for activity, and those able to walk or fly within 1 h were considered recovered. Control experiments showed that water spotted on the Whatman paper had no effect on the flies, and that pre-treating the paper with 10 mM NaOH completely prevented any subsequent toxicity of KCN, indicating the paper was sufficiently acidic to generate HCN. Consistent with the latter point, it was shown in control experiments that by leaving the filter paper in the vial for 1 h KCN spotted on the paper in 4 M NaOH in the bottom of the vial (the filter paper was suspended in the vial and did not contact the NaOH) could be quantitatively recovered. Since not all of the KCN was necessarily released as HCN during the 1 min exposure of the flies, and since some of the generated HCN gas could condense into liquid at room temperature, the stated concentrations of HCN gas represent the maximal to which the flies were exposed.

Injection with KCN. Anesthetized flies were injected with 1 µl of 10 mM $Na_2CO_3$, pH 9.5, or 1 µl 100 µM KCN dissolved in the $Na_2CO_3$ solution as described above for injection with cobinamide or cobalamin.

Measurement of HCN. Cyanide gas generated in vials was measured by collecting the HCN in 0.2 ml of 100 mM NaOH in the bottom of the vials, being careful not to allow the paper containing the KCN to contact the NaOH. Cyanide in flies was measured by extracting flies in 500 µl 100 mM NaOH. In both cases, the resulting NaCN was measured as described originally by Guilbault and Kramer, and modified by Gewitz et al, i.e., the NaCN was incubated with p-nitrobenzaldehyde and o-dinitrobenzene, and the colored product was measured at 578 nm (Guilbault and Kramer, *Anal. Chem.* 28: 834-836, 1966; Gewitz et al., *Planta (Berl.)* 131: 145-148, 1976). The assay was linear between 1 and 15 µM NaCN.

Effect of KCN on Malpighian Tubule Secretion in *D. Melanogaster*. The Malpighian tubules of *D. Melanogaster* are the insect's fluid transporting and osmoregulatory organ, corresponding to vertebrate kidneys. Tubular secretion rates were measured as described previously (Broderick et al., *J. Biol. Chem.* 280: 8678-8685, 2005). Briefly, the two pairs of Malpighian tubules of a fly were dissected from 10 adult flies who had been grown on either standard food or food containing 100 µM cobinamide or cobalamin. Each tubule pair with its accompanying ureter was suspended in mineral oil, with the non-ureteral end of one tubule bathed in a 10 µl droplet of Schneider's Insect medium, and the corresponding end of the other tubule immobilized on a dissecting pin. The amount of fluid transported by the tubule bathed in Schneider's medium was determined every 10 min at room temperature by measuring the size of drops formed at the end of the ureter. After measuring basal fluid secretion rates over three 10 min intervals, KCN was added at a final concentration of 100 µM to the droplet of Schneider's medium, and rates of fluid secretion were measured for an additional three 10 min intervals. In some experiments, cobinamide at a final concentration of 100 µM was added 10 min after the KCN.

2. Results

Cobinamide Recovers Respiratory Activity in Cyanide-Treated Chinese Hamster Cells. It was shown previously that measuring respiratory activity in permeabilized Chinese hamster cells incubated with succinate and glycerol 3-phosphate accurately reflects activity of cytochrome c oxidase, i.e., complex IV of the mitochondrial electron transport chain (Way, *Annu. Rev. Pharmacol. Toxicol.* 24: 451-481, 1984).

Figure 8:
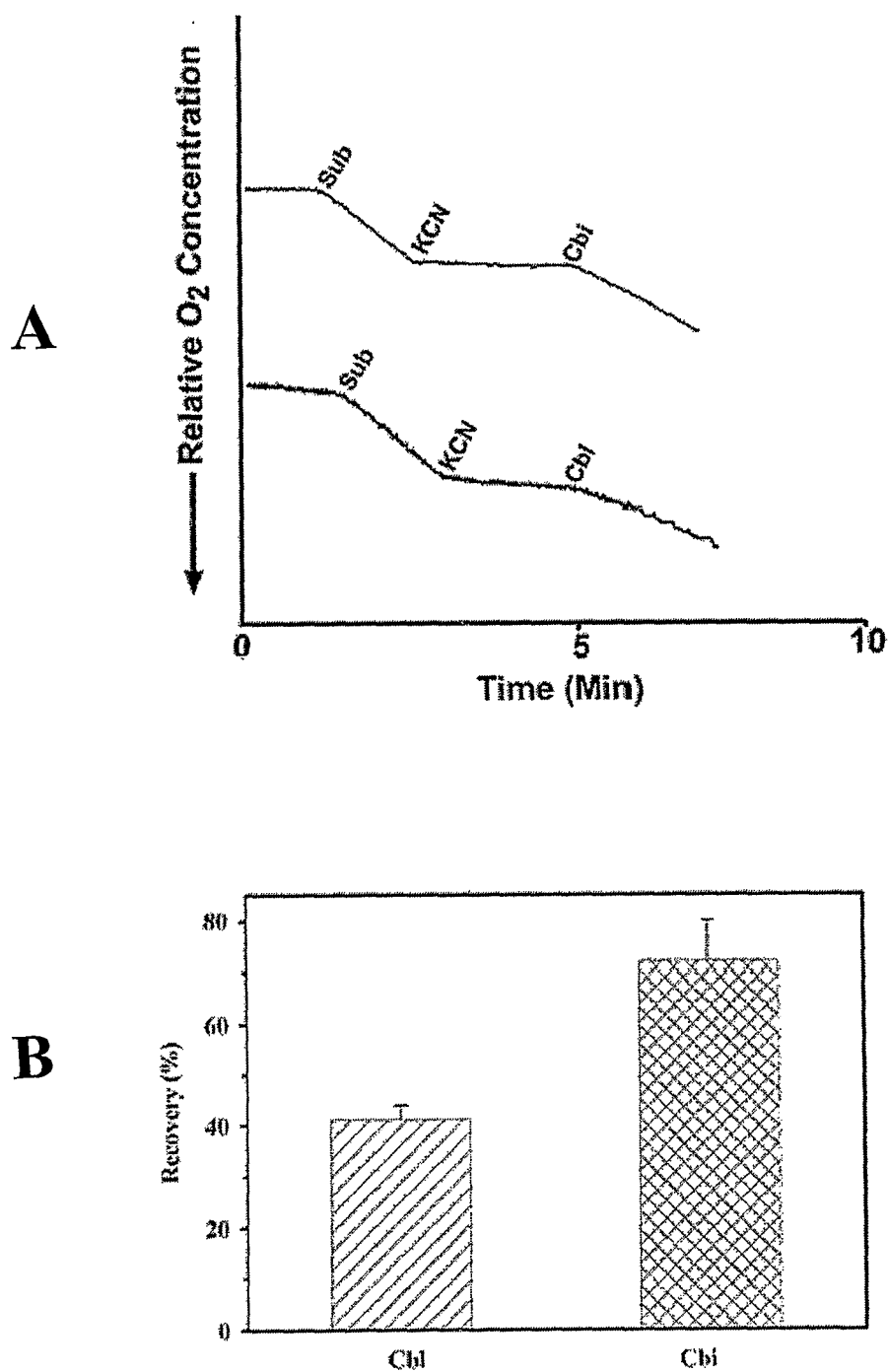
FIG. 8. Cobinamide Recovers Respiratory Activity in Cyanide-Treated Chinese Hamster Cells. Chinese hamster cells at a density of approximately $3\times10^7$ cells/ml were transferred to a metabolic chamber, and respiratory activity was assessed by measuring oxygen consumption using an oxygen electrode. In the absence of added substrate (sub, 5 mM sodium succinate and 5 mM glycerol 3-phosphate), oxygen consumption was low—as indicated by the almost horizontal lines on the tracings in panel a. KCN, cobinamide (Cbi), and cobalamin (Cbl) were added to final concentrations of 250 µM at the indicated times. In panel a are shown two representative tracings plotted on the same graph, and in Panel B is shown the percent recovery by cobinamide and cobalamin; the latter data are a summary of at least five independent experiments performed in duplicate (mean ±S.D.).

Cyanide is an effective inhibitor of cytochrome c oxidase, and it was found that 250 µM KCN almost completely inhibited respiratory activity in Chinese hamster cells (FIG. 8a). At physiologic pH, KCN will be converted to HCN since the pKa of the latter is 9.3; although the boiling point of HCN is 25.7° C. and the experiments were performed at 37° C., it is unlikely that any of the generated HCN escaped from the buffer since the incubation chamber was completely filled with buffer prior to starting the experiment. Adding cobinamide at an equimolar concentration as KCN induced a rapid recovery of respiration to about 75% of the control non-KCN-treated cells (FIG. 8a, upper tracing, and FIG. 8b, cross-hatched bar). On an equimolar basis, cobalamin was considerably less potent than cobinamide, inducing a 42% recovery of respiration (FIG. 8a, lower tracing, and FIG. 8b, left diagonal stripped bar). Neither cobinamide nor cobalamin alone had any effect on oxygen consumption.

Cobinamide Restores Growth in Cyanide-Treated Chinese Hamster Cells. Mammalian cells in culture derive much of their ATP from glycolysis, and if oxidative phosphorylation is inhibited, the cells will switch to anaerobic metabolism (Scheffler, I. 1986. Carbohydrate Metabolism in Cultured Cells. Plenum Press, New York. 77-109 pp). Thus, to study the effect of cyanide on cell growth, glucose-free medium containing galactose as a sugar source (Soderberg et al., *Somat. Cell Genet.* 5: 225-240, 1979). Because under physiologic conditions KCN will be converted to HCN, and HCN is volatile, KCN needed to be added serially to cultured cells to observe growth inhibition. Treating Chinese hamster cells with 100 µM KCN at zero time, eight, and 24 h, inhibited growth at 48 h by 31±5% (mean ±S.D. of three independent experiments) was used. Adding 10 µM cobinamide at zero time to the KCN-treated cells restored their growth rate to normal. Presumably the reason such a low amount of cobinamide was effective is that most of the generated HCN vaporized from the culture medium. Similar results were found for 10 µM cobalamin.

Figure 9:
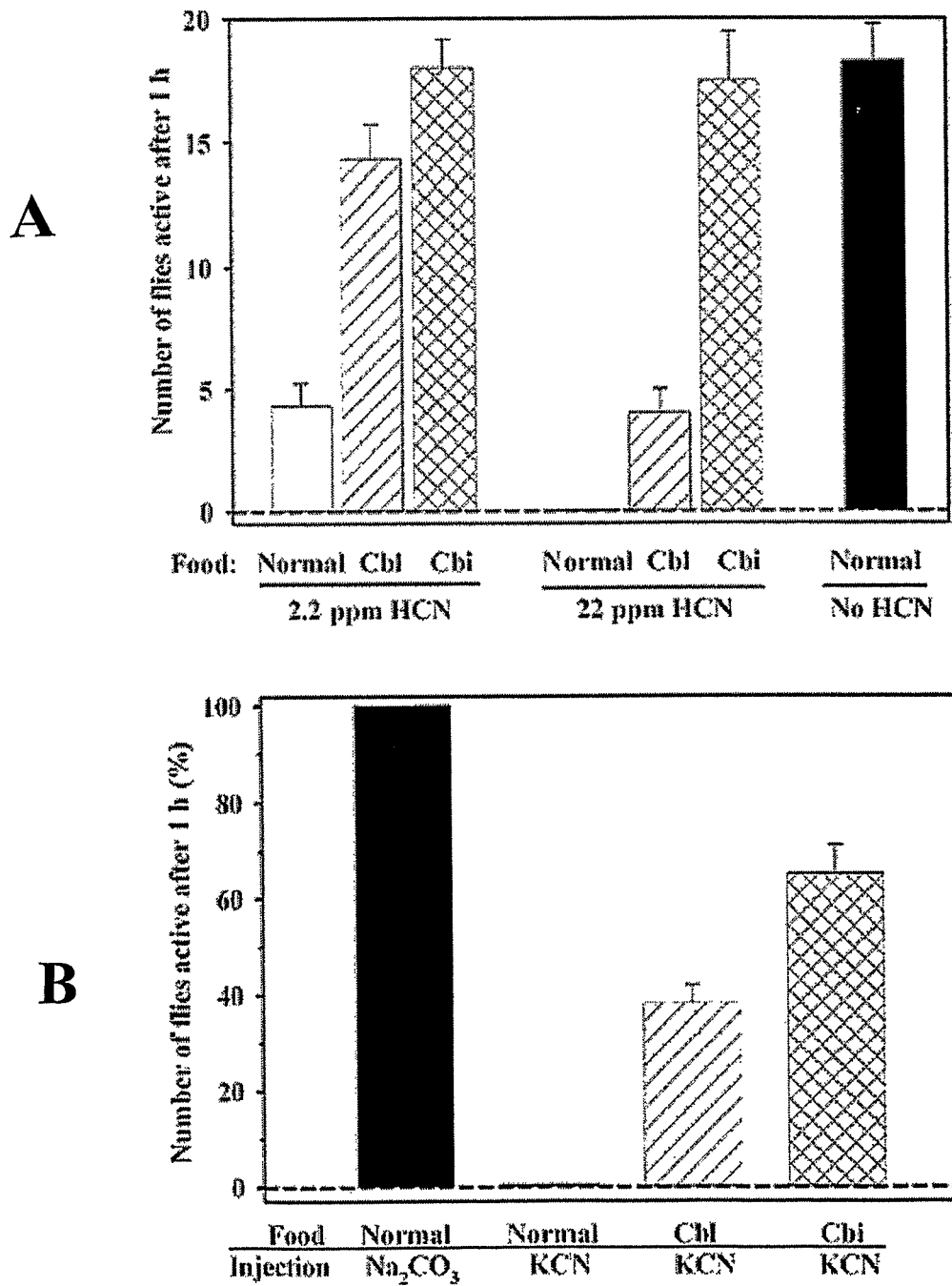
FIG. 9. Cobinamide Ingestion Detoxifies Cyanide Gas and KCN in *D. Melanogaster*. Flies were grown from the first instar larval stage on standard fly food paste (Normal food, open and filled bars), or standard food containing either 100 µM cobalamin (Cbl, left-diagonal striped bars) or 100 µM cobinamide (Cbi, cross-hatched bars). Panel A. Under each indicated condition, 20 flies were exposed for 1 min to HCN at either 2.2 ppm or 22 ppm. The HCN caused all flies to collapse motionless within 20 sec; plotted on the ordinate is the number of flies that recovered and were able to walk or fly by 1 h post exposure. Flies not exposed to HCN are shown in the filled bar on far right. Panel B. Approximately 10 flies under each condition were injected with 1 µl of either 10 mM $Na_2CO_3$, pH 9.5 (filled bar) or 100 µM KCN in $Na_2CO_3$ as indicated. The data are presented as the percentage of flies active after 1 h. The data in both panels are the mean ±S.D. of at least three independent experiments performed in duplicate.

Cobinamide Detoxifies Cyanide Gas in *D. Melanogaster*. Delivery of Cobinamide Via Ingestion. *D. melanogaster* is now recognized as an excellent model for human disease, and is used increasingly in drug discovery (Tickoo and Russell, *Curr. Opin. Pharmacol.* 2: 555-560, 2002). As a flying insect, *D. melanogaster* has a relatively high metabolic rate; it would, thereof, be expected to be highly sensitive to HCN, which could enter flies within seconds through their spiricle-tracheal respiratory system, and more slowly over minutes through trans-cuticle transport (Biology of *Drosophila*, John Wiley & Sons, Inc., New York, 1950). A 1 min exposure to an HCN concentration as low as 2.2 ppm induced death in 80% of flies, and that at 22 ppm, all flies died (FIG. 9a, open bar, and solid line at zero value on y axis, respectively, for flies grown on normal food). At the low and high exposure levels, the HCN concentration in the flies was found to be approximately 1 and 10 µM, respectively, based on a total water volume in *D. melanogaster* of about 10 µl (Biology of *Drosophila*, John Wiley & Sons, Inc., New York, 1950). When flies were grown for several days on food containing 100 µM cobinamide and then exposed to HCN, approximately 90% of them survived the gas exposure, both at 2.2 and 22 ppm (FIG. 9a, cross-hatched bars). Survival of the cobinamide-fed flies was similar to that of control flies not exposed to HCN, but handled in a similar fashion as the cyanide-exposed flies (FIG. 9a, filled bars). Thus, compared to appropriate control flies, cobinamide induced complete recovery of the cyanide-exposed flies. This is to be contrasted with flies fed 100 µM cobalamin, which exhibited 80% recovery at 2.2 ppm HCN, but only 20% recovery at 22 ppm (FIG. 9a, left-diagonal striped-bars). Cobinamide was, therefore, much more effective than cobalamin at detoxifying cyanide in *D. melanogaster*. The concentrations of cobinamide and cobalamin achieved in the flies could not be determined because it was below the limits of detection of the high performance liquid chromatography system described in Methods (100 pmol).

The cobinamide-fed flies could be exposed to 22 ppm HCN for up to 15 min without any significant increase in mortality, but exposure times>30 min resulted in death of all flies. This suggests that in addition to entering through the respiratory system, HCN can, during more prolonged exposure, enter the flies through other mechanisms, for example a trans-cuticle mechanism, thereby achieving higher intra-organismal levels.

As an alternative method of exposing flies to cyanide, flies were injected with 1 µl of 100 µM KCN dissolved in 10 mM $Na_2CO_3$, pH 9.5. Assuming the KCN was evenly distributed in the flies, intracellular KCN concentrations of about 10 µM should have been achieved, which is very similar to the concentrations achieved in flies exposed to 22 ppm HCN. Injecting $Na_2CO_3$ alone had no effect on the flies (FIG. 9b, solid bar), whereas injecting KCN resulted in 100% mortality (FIG. 9b, solid line at zero value on y axis). Flies grown on 100 µM cobinamide were relatively resistant to the KCN exhibiting a 65% survival rate (FIG. 9b, cross-hatched bar), while flies grown on 100 µM cobalamin exhibited a 38% survival rate (FIG. 9b, left diagonal bar). The difference between cobinamide and cobalamin was statistically significant ($p<0.01$).

Delivery of Cobinamide Via Injection. Because the concentration of cobinamide and cobalamin achieved in the flies in the ingestion studies could not be measured, the flies were injected with 1 µl of 500 µM cobinamide and cobalamin, yielding approximate concentrations in the flies of 50 µM, and then exposed the flies to 22 ppm HCN. This concentration of HCN killed almost all flies injected with water (FIG. 10a, open bar), similar to our previous findings. This is to be contrasted with flies injected with cobinamide and cobalamin, of which 65% and 44% survived, respectively (FIG. 10a, cross-hatched bar and left-diagonal bar on left, respectively); the difference between cobinamide and cobalamin was statistically significant at $p<0.05$.

In the treatment of HCN exposure, it would be most useful to have a detoxifying agent which could be used post-exposure, rather than pre-exposure, therefore, the protocol was modified and the flies were exposed to HCN first, followed by injecting them with water, cobinamide, or cobalamin. Cobinamide salvaged 94% and cobalamin 62% of flies exposed to HCN, whereas water-injected flies all died (FIG. 10a, cross-hatched bar and left-diagonal bar on right, respectively, compared to solid line at zero value on y axis). Once again, the difference between cobinamide and cobalamin was statistically significant ($p<0.05$). The reason for higher survival rates when cobinamide and cobalamin were administered post-HCN-exposure, compared to pre-HCN-exposure, can reflect a procedural difference: in the pre-HCN-exposure experiments, the flies had to be anesthetized on ice prior to injection with cobinamide/cobalamin, and then allowed to recover for 10 min, whereas in the post-HCN-exposure experiments, the flies were injected immediately with cobinamide/cobalamin post HCN exposure because they were already unconscious. The anesthetization procedure in the pre-HCN-exposure experiments could have decreased subsequent survival or cobinamide/cobalamin could have been partially excreted during the 10 min recovery period. High survival rates when cobinamide and cobalamin are administered post HCN exposure would be clinically advantageous.

Figure 10:
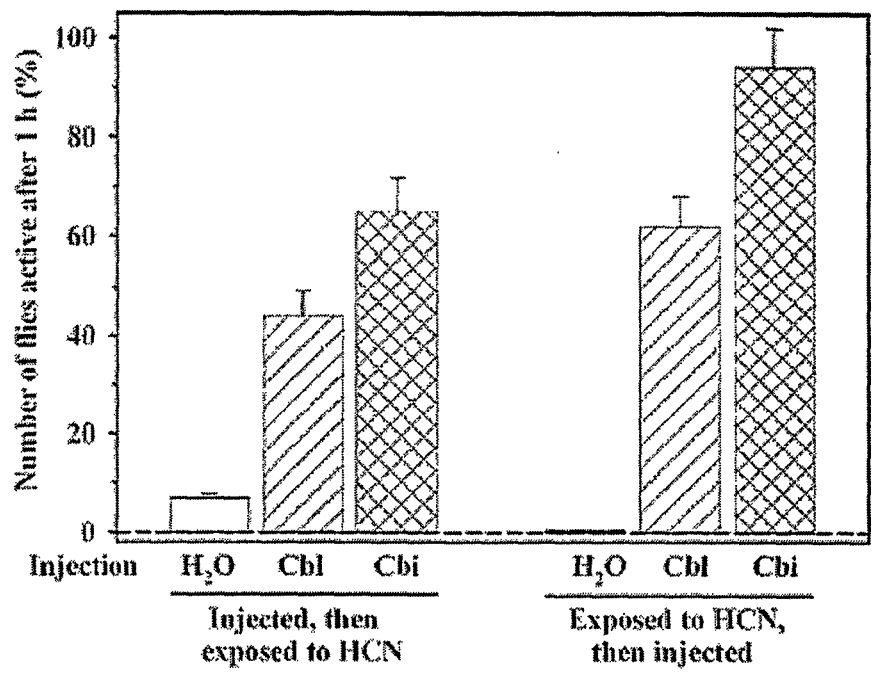
FIG. 10. Cobinamide Injection or Inhalation Detoxifies Cyanide Gas in *D. Melanogaster*. Flies received water (open and filled bars), cobalamin (Cbl, left-diagonal striped bars), or cobinamide (Cbi, cross-hatched bars) by either injection (1 µl of water or 500 µM Cbl or Cbi, Panel A) or inhalation using a nebulizer containing water or 100 µM of Cbl or Cbi (Panel B). The flies were exposed for 1 min to HCN at 22 ppm (Panel A) or 2.2 ppm (Panel B) either before receiving the cobinamide or cobalamin (bars in right half of panels) or after receiving the cobinamide or cobalamin (bars in left half of panels). Flies nebulized with water, but not exposed to HCN are shown in the filled bar in Panel B. The data are the mean ±S.D. of at least three independent experiments performed in duplicate.
Figure 10:
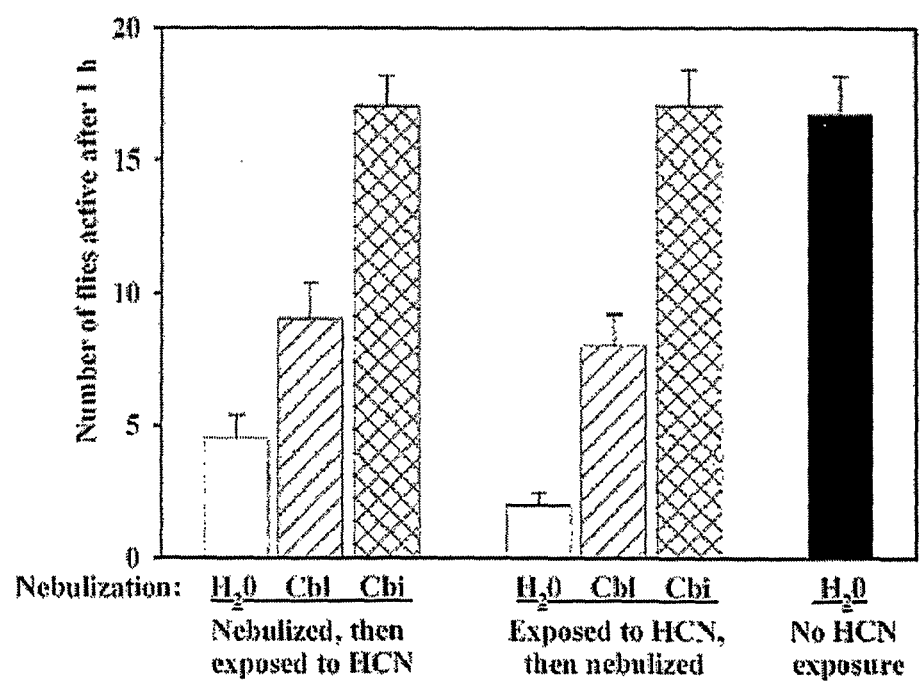

Delivery of Cobinamide Via Inhalation. In acute cyanide gas exposure, administering cobinamide via the gastrointestinal route would unlikely result in sufficiently rapid absorption to be effective, and administering cobinamide via injection would require the presence of trained health personnel. Cobinamide was tested and could reduce cyanide toxicity when provided via inhalation, since this mode of delivery is simple and rapid. A system was developed using a hand-held nebulizer to deliver drugs to flies via inhalation, and showed using the red dye amaranth that the dye was delivered to internal organs via the flies' spiricle-tracheal system. To our knowledge, no previous workers have administered drugs to *D. melanogaster* via nebulization. Even at low flow rates, nebulization of water killed about 20% of control non-cyanide exposed flies, presumably because of turbulent air flow and shear forces (FIG. 10b, filled bar). When flies were exposed to 2.2 ppm HCN after nebulization of water, 80% of the flies died (FIG. 10b, pen bar on left), similar to mortality rates found previously at this HCN concentration (FIG. 9a). This is to be contrasted to only an 18% mortality rate in flies which received cobinamide by nebulization prior to HCN exposure (FIG. 10b, cross-hatched bar on left). Since the latter survival rate is similar to that of the control non-cyanide exposed flies receiving nebulized water, the data suggest that cobinamide completely prevented mortality. Flies which received cobalamin by nebulization exhibited some protection from HCN with a 55% mortality rate (FIG. 10b, left-diagonal bars on left).

As mentioned above, cobinamide would be most useful in cases of cyanide gas exposure if it could be administered post exposure, rather than pre exposure. Therefore, the protocol was altered and flies were exposed to 2.2 ppm HCN, and then subjected them to nebulization with water, cobalamin, or cobinamide. Cobinamide was found as effective in preventing death under these conditions as it was when administered prior to cyanide exposure (FIG. 10b, cross-hatched bar on right). Cobalamin also exhibited similar results as when it was administered prior to cyanide exposure, but flies nebulized with water showed lower survival rates, presumably because they were already impaired from the cyanide at the time of nebulization (FIG. 10b, open and left-diagonal bars on right, respectively).

Figure 11:
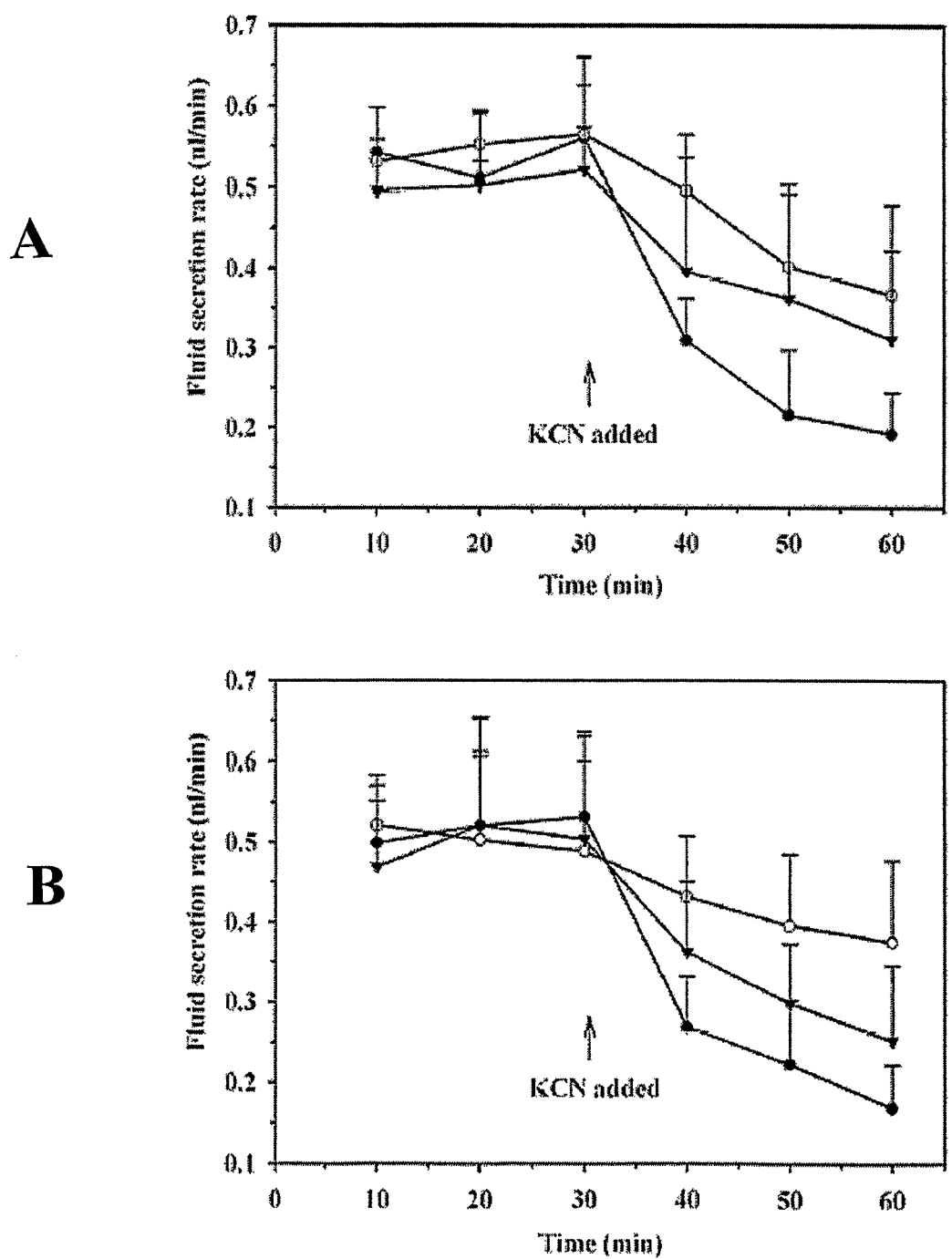
FIG. 11. Cobinamide Reduces Cyanide Inhibition of Malpighian Tubule Secretion. Pairs of Malpighian tubules were removed from *D. melanogaster*, and rates of fluid secretion were determined by measuring droplet formation from the ureter over 10 min intervals. Secretion rates were measured for three 10 min intervals prior to adding 100 µM KCN to all the tubules. Panel A. Cobinamide (open circles) and cobalamin (triangles) at concentrations of 100 µM were added to the tubules at zero time. Panel B. Flies were grown from the first instar larval stage on standard fly food (closed circles) or food containing either 100 µM cobinamide (open circles) or 100 µM cobalamin (triangles) prior to removal of their Malpighian tubules. Panel C. Cobinamide at a concentration of 100 µM was added to the tubules 10 min after adding KCN (open circles). Data are the mean ±S.D. of at least three independent experiments performed on 20 pairs of Malpighian tubules.
Figure 11:
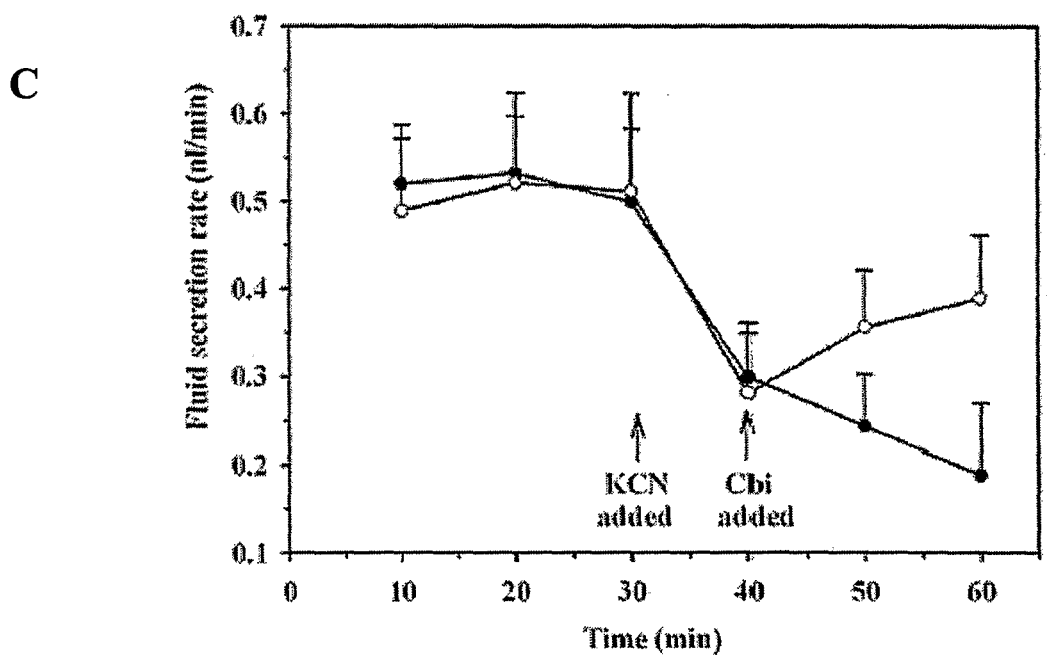

Cobinamide Reduces Cyanide Inhibition of Malpighian Tubule Secretion. Secretion by insect Malpighian tubules is an ATP-dependent process, and, therefore, would be expected to be inhibited by cyanide (Dow and Davies, *Physiol Rev.* 83: 687-729, 2003). 100 µM KCN rapidly reduced rates of tubular secretion by *D. melanogaster* Malpighian tubules (FIG. 11a, filled circles). Tubules that had been treated at time zero with either 100 µM cobinamide or 100 µM cobalamin showed significant resistance to the inhibitory effect of KCN (FIG. 11a, open circles and triangles, respectively). Cobinamide and cobalamin had no effect on basal secretion rates as can be observed during the zero to 30 min interval. When the same experiment was performed on flies which had been grown on cobinamide prior to removing the Malpighian tubules and measuring tubular secretion rates, almost complete reversal of the toxic effects of KCN was found (FIG. 11b, compare open circles, cobinamide-fed flies to filled circles, control flies). The more complete reversal of KCN toxicity in the cobinamide-fed flies compared to the cobinamide-treated tubules can have been from slow cellular uptake of cobinamide in the latter condition; longer times of cobinamide pre-incubation with the tubules could not be done because the tubules have a limited experimental time. Flies which had been grown on cobalamin showed an intermediate degree of resistance to KCN (FIG. 11b, triangles).

To determine if cobinamide could reverse the inhibitory effects of cyanide on tubular secretion, cobinamide was added 10 min after adding 100 µM KCN to the tubules, and found that tubular secretion rates increased significantly (FIG. 11c, open circles are cobinamide-treated tubules). Even after only 10 min of cyanide exposure, morphological changes in the tubular cells were observed, and this could explain why cobinamide did not return tubular secretion to normal.

3. Discussion

Previous workers have shown that HCN, the form of cyanide present at physiological pH, reacts with purified cytochrome c oxidase in two steps: relatively rapid formation of an enzyme-HCN intermediate, followed by slow conversion of the intermediate to a stable product, possibly an enzyme-cyanide ion complex (van Buuren et al., *Biochim. Biophys. Acta* 256: 258-276, 1972; Panda and Robinson, *Biochemistry* 34: 10009-10018, 1995). The rate constant for the first step is 0.03 sec-1, yielding a half-life of the intermediate of 23 seconds (van Buuren et al., *Biochim. Biophys. Acta* 256: 258-276, 1972; Panda and Robinson, *Biochemistry* 34: 10009-10018, 1995). Dissociation of cyanide from the final product is estimated to be very slow, $\approx 10^{-6}$ sec$^{-1}$, and thus the overall reaction of cyanide with cytochrome c oxidase has been referred to as irreversible or "quasi-reversible" (van Buuren et al., *Biochim. Biophys. Acta* 256: 258-276, 1972; Panda and Robinson, *Biochemistry* 34:10009-10018, 1995). Using cobinamide and cobalamin, both of which have relatively high affinities for cyanide, the reaction of cyanide with cytochrome c oxidase was found to be reversible, as demonstrated by measuring enzyme activity in permeabilized Chinese hamster cells. In addition, cobinamide and cobalamin reversed the lethal effects of cyanide in the hamster cells and in *D. melanogaster*, and cobinamide largely reversed cyanide inhibition of Malpighian tubular transport, an ATP-dependent process. Assuming these latter effects of cyanide were from inhibition of cytochrome c oxidase, these data provide evidence that the reaction of cyanide with cytochrome c oxidase is reversible when assessed in intact organisms or organ systems. Similar conclusions have been drawn from previous workers using cobalamin in other animal models of cyanide poisoning and in the treatment of patients suffering from smoke inhalation (Fortin et al., JEMS 29: suppl-21, 2004; Hall and Rumack, *J. Emerg. Med.* 5: 115-121, 1987; Posner et al., *Anesthesiology* 44: 157-160, 1976; Mushett et al., *Proc. Soc. Exp. Biol. Med.* 81: 234-237, 1952).

As a first approximation, cyanide detoxification by cobinamide and cobalamin should follow their relative affinity constants for cyanide, indicating that cobinamide, with 1010 higher affinity for cyanide than cobalamin, should be a more effective cyanide detoxifying agent than cobalamin. However, intracellular proteins can bind cobinamide and cobalamin to varying degrees and prevent deriving a clear relationship between binding constants and detoxifying effect. Nevertheless, in almost all experiments performed, cobinamide more effectively detoxified cyanide than cobalamin, suggesting a direct relation between binding affinities and efficacy.

Blood cyanide levels range from 2-250 µM in smoke inhalation victims, with levels above 40 µM associated with high mortality rates (Baud et al., *N. Engl. J. Med.* 325: 1761-1766, 1991). These data correlate well with animal studies which have shown LD50's for blood cyanide in the range of 20-100 µM, depending on the animal species (Salkowski and Penney, *Vet. Hum. Toxicol.* 36: 455-466, 1994). The standard dose of cobalamin for smoke inhalation patients is five grams given intravenously, which yields a mean peak serum concentration of about 650 µM (Fortin et al., *JEMS* 29:suppl-21, 2004; Forsyth et al., *J. Toxicol. Clin. Toxicol.* 31: 277-294, 1993). Because cobinamide was found more effectively detoxified cyanide than cobalamin, one would expect that lower amounts of cobinamide could be used to treat smoke inhalation victims.

When developing responses to weapons of mass destruction, it would be helpful to have drugs which could be administered after exposure to the toxic agent, since, in general, prophylactic treatment may not be possible. It was, therefore, useful to find that cobinamide could be given to flies after cyanide exposure, and was at least as effective as when given prior to cyanide exposure. Of perhaps even greater importance, cobinamide could be administered by injection or inhalation, which would allow for rapid drug delivery.

Recent data suggest that cyanide can play a role in the development of several diseases. Cigarette smokers have high levels of blood and urinary cyanide and thiocyanate levels, as do patients on hemodialysis (Abou-Seif, *J. Biochem. Toxicol.* 11: 133-138, 1996; Hasuike et al., 19: 1474-1479, 2004). In both cases, the high thiocyanate levels can contribute to lipid oxidation, and therefore, arteriosclerosis, because thiocyanate is a preferred substrate for peroxidase enzymes (Zhang et al., *Blood* 99: 1802-1810, 2002; van Dalen and Kettle, *Biochem. J.* 358: 233-239, 2001; Scanlon et al., *Atherosclerosis* 121: 23-33, 1996; Exner et al., *Free Radic. Biol. Med.* 37: 146-155, 2004). Mucoid *Pseduomonas aeruginosa* are cyanogenic, and bacteria isolated from sputum of cystic fibrosis patients have been shown to produce cyanide (Carterson et al., *J. Bacteriol.* 186: 6837-6844, 2004). Thus, it is possible that cyanide contributes to the lung destruction in cystic fibrosis patients infected with *P. aeruginosa* (Carterson et al., *J. Bacteriol.* 186: 6837-6844, 2004). For these clinical conditions it would be useful to have a drug which could detoxify cyanide, particularly one which could be administered by inhalation in the case of cystic fibrosis.

As a precursor in the biosynthesis of cobalamin, cobinamide is a contaminant of multivitamin preparations, and at least in pigs, cobinamide can be absorbed across the ileum independently of intrinsic factor (Kondo et al., *J. Clin. Invest* 70: 889-898, 1982; Kanazawa et al., *Proc. Soc. Exp. Biol. Med.* 183: 333-338, 1986). Once absorbed, cobinamide binds tightly to haptocorrin previously referred to as R protein as well as transcobalamin I and III), but poorly to transcobalamin II (Fedosov et al., *J. Biol. Chem.* 277: 9989-9996, 2002; Ermens et al., *Clin. Biochem.* 36: 585-590, 2003; Fedosov et al., *Biochemistry* 34:16082-16087, 1995). Since the serum levels of haptocorrin and transcobalamin II are similar, a significant amount of cobinamide could be present in serum, and cobalamin analogs, including cobinamide, have been detected in the serum, bile, and tissues of animals and humans, accounting for 5-50% of total corrinoids (Ermens et al., *Clin. Biochem.* 36: 585-590, 2003; Kolhouse et al., *N. Engl. J. Med.* 299: 785-792, 1978; el Kholty et al., *Gastroenterology* 101: 1399-1408, 1991; Kondo et al., *Proc. Natl. Acad. Sci. U.S.A* 77: 817-821, 1980; Baker et al., *J. Am. Coll. Nutr.* 5: 467-475, 1986). Intravenous injection of tracer amounts of radioactive cobinamide into rabbits indicates that cobinamide, like cobalamin, is taken up by the liver within minutes, but unlike cobalamin, cobinamide is released more slowly from the liver with a t? of ?150 hours; once released from the liver, the tissue distribution of cobinamide and cobalamin were similar, and they were both excreted in the urine and feces (Kolhouse and Allen, *J. Clin. Invest* 60: 1381-1392, 1977). Thus, with a few notable exceptions, cobinamide and cobalamin appear to be handled similarly in mammalian systems.

At concentrations of 3.7 nM and 200 µM, cobinamide had no growth inhibitory effects on mouse leukemic cells, and human monocytes and lymphocytes, respectively (Kondo et al., *Int. J. Hematol.* 56: 167-177, 1992; Weinberg et al., *Biochem. Biophys. Res. Commun.* 246: 393-397, 1998). In whole animals, cobinamide had no effect on the growth of baby chicks when administered parenterally at 40 times the dose of cobalamin; it did inhibit chick growth when given orally suggesting it interfered with cobalamin absorption (Coates et al., *Biochem. J.* 64: 682-686, 1956). Similarly, when cobinamide was administered subcutaneously to rats at a continual rate of 4 µg/h for 14 d, there were no apparent toxic effects, nor did cobinamide inhibit the two mammalian cobalamin-dependent enzymes methionine synthase or methylmalonyl-CoA mutase (Stabler et al., *J. Clin. Invest.* 87: 1422-1430, 1991). Cobinamide is not toxic to cultured mammalian cells up to at least 50 µM, and that its toxicity could be reversed completely by cobalamin (Broderick et al., *J. Biol. Chem.* 280: 8678-8685, 2005). Cobinamide was found to have no effect on the activities of methionine synthase or methylmalonyl-CoA mutase, suggesting that cobinamide was interfering with cobalamin metabolism (Broderick et al., *J. Biol. Chem.* 280: 8678-8685, 2005). Administering cobalamin with cobinamide should prevent any toxicity, and adding cobalamin to cobinamide should be beneficial in detoxifying cyanide.

Cobinamide is a highly effective agent for detoxifying cyanide. It can be used potentially in a variety of clinical states, and can be particularly beneficial as an antidote to massive cyanide poisoning (i.e., as a result of an industrial accident or an attack using WMD).

What is claimed:

1. A method for delaying or inhibiting a disease state in a subject caused or exacerbated by the presence of excess cyanide in the subject in need thereof comprising: administering a pharmaceutically effective amount of cobinamide.

2. The method of claim 1, wherein the subject is a cigarette smoker.

3. The method of claim 1, wherein the excess cyanide is brought about by smoke inhalation, exposure to nitroprusside, or exposure to an industrial accident.

4. The method of claim 1, wherein the excess cyanide is brought about by weapons of mass destruction.

5. The method of claim 1, wherein the cobinamide is administered at a dose of 1 to 500 mg.

6. A method for alleviating the symptoms of a disease state in a subject caused or exacerbated by the presence of excess cyanide in the subject in need thereof comprising administering a pharmaceutically effective amount of cobinamide, wherein the subject is diagnosed as suffering from or at risk of developing a disease state caused or exacerbated by the presence of excess cyanide.

7. The method of claim 6, wherein the subject is a cigarette smoker.

8. The method of claim 6, wherein the excess cyanide is brought about by smoke inhalation, exposure to nitroprusside, or exposure to an industrial accident.

9. The method of claim 6, wherein the excess cyanide is brought about by weapons of mass destruction.

10. The method of claim 6, wherein the cobinamide is administered at a dose of 100 mg to 1 g.

11. A method for delaying or inhibiting cyanide toxicity in a subject in need thereof comprising administering a pharmaceutically effective amount of cobinamide to the subject.

12. The method of claim 11, wherein the cobinamide is administered at a dose of 100 mg to 1 g.

13. The method of claim 1, wherein cobinamide is administered at a dose of 100 mg to 1 g or 500 mg to 5 g.

14. The method of claim 1, wherein the excess cyanide is brought about by smoke inhalation.

15. The method of claim 1, wherein cobinamide is administered in a pharmaceutical composition with a pharmaceutically acceptable carrier.

16. The method of claim 1, wherein cobinamide is administered intramuscularly.

17. The method of claim 1, wherein cobinamide is administered intravenously, subcutaneously, or via inhalation.

18. The method of claim 1, wherein cobinamide is administered with a pharmaceutically acceptable excipient.

19. The method of claim 6, wherein cobinamide is administered at a dose of 1 to 500 mg or 500 mg to 5 g.

20. The method of claim 6, wherein the excess cyanide is brought about by smoke inhalation.

21. The method of claim 6, wherein cobinamide is administered in a pharmaceutical composition with a pharmaceutically acceptable carrier.

22. The method of claim 6, wherein cobinamide is administered intramuscularly.

23. The method of claim 6, wherein cobinamide is administered intravenously, subcutaneously, or via inhalation.

24. The method of claim 6, wherein cobinamide is administered with a pharmaceutically acceptable excipient.

25. The method of claim 11, wherein cobinamide is administered at a dose of 1 to 500 mg or 500 mg to 5 g.

26. The method of claim 11, wherein the cyanide toxicity is brought about by smoke inhalation, exposure to nitroprusside, or exposure to an industrial accident.

27. The method of claim 11, wherein cobinamide is administered in a pharmaceutical composition with a pharmaceutically acceptable carrier.

28. The method of claim 11, wherein cobinamide is administered intramuscularly.

29. The method of claim 11, wherein cobinamide is administered intravenously, subcutaneously, or via inhalation.

30. The method of claim 11, wherein cobinamide is administered with a pharmaceutically acceptable excipient.

\* \* \* \* \*